United States Patent
Shirasuna et al.

(10) Patent No.: US 11,280,720 B2
(45) Date of Patent: Mar. 22, 2022

(54) CELL ANALYSIS METHOD, CELL ANALYZER AND SAMPLE SCREENING METHOD

(71) Applicant: Sysmex Corporation, Kobe (JP)

(72) Inventors: Kei Shirasuna, Kobe (JP); Ryuichiro Ebi, Kobe (JP); Shigeki Abe, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 16/694,058

(22) Filed: Nov. 25, 2019

(65) Prior Publication Data

US 2020/0096433 A1    Mar. 26, 2020

Related U.S. Application Data

(63) Continuation of application No. 14/508,522, filed on Oct. 7, 2014, now abandoned.

(30) Foreign Application Priority Data

Oct. 11, 2013    (JP) .................................. 2013-213930

(51) Int. Cl.
| | |
|---|---|
| *G01N 15/14* | (2006.01) |
| *G01N 21/49* | (2006.01) |
| *G01N 15/10* | (2006.01) |
| *G16B 30/00* | (2019.01) |
| *C12Q 1/6886* | (2018.01) |

(52) U.S. Cl.
CPC ......... *G01N 15/147* (2013.01); *C12Q 1/6886* (2013.01); *G01N 15/1431* (2013.01); *G01N 21/49* (2013.01); *G16B 30/00* (2019.02); *G01N 2015/1006* (2013.01); *G01N 2015/1402* (2013.01); *G01N 2015/1477* (2013.01)

(58) Field of Classification Search
None
See application file for complete search history.

(56) References Cited

U.S. PATENT DOCUMENTS

| | | | | |
|---|---|---|---|---|
| 5,100,622 A | * | 3/1992 | Mimura | G01N 35/00594 356/73 |
| 2003/0113925 A1 | * | 6/2003 | Gordon | G01N 15/1475 506/3 |
| 2008/0262384 A1 | * | 10/2008 | Wiederkehr | G01N 33/57411 600/569 |
| 2009/0091746 A1 | | 4/2009 | Fukuda | |
| 2011/0014685 A1 | | 1/2011 | Fukuda | |
| 2012/0052491 A1 | * | 3/2012 | Shioyama | G01N 15/1459 435/6.1 |
| 2012/0148142 A1 | * | 6/2012 | Ortyn | G01N 15/1475 382/133 |

FOREIGN PATENT DOCUMENTS

| | | |
|---|---|---|
| EP | 2 261 632 A1 | 12/2010 |
| EP | 2 345 885 A2 | 7/2011 |
| EP | 2 620 767 A1 | 7/2013 |
| EP | 2 645 083 A2 | 10/2013 |
| EP | 2645082 A2 | 10/2013 |
| EP | 2645082 A3 | 12/2013 |
| EP | 2 698 622 A2 | 2/2014 |
| EP | 2 735 872 A1 | 5/2014 |
| WO | WO 2013/015089 A1 | 1/2013 |

OTHER PUBLICATIONS

Prewitt, J.M.S. Mathematical methods applied to image processing in medicine. In: Lecture Notes in Medical Informatics. Copyright 1981. Online Conferences, Ltd., Uxbridge, England. Eds: D.A.B. Lindberg and P.L. Reichertz. specif, pp. 40, 42, 43.*
BD Biosciences. Apr. 2000. Introduction to flow cytometry: a learning guide. Copyright 2000. Becton, Dickinson and Company. San Jose, CA. pp. 1-52. specif, p. 36.*
Cibas, E.S. Cervical and Vaginal Cytology. In: Cytology: Diagnostic principles and clinical correlates. Third Edition. Copyright 2009. Saunders, an imprint of Elsevier, Inc. Eds.: Edmund S. Cibas and Barbara S. Ducatman. Philadelphia, PA. pp. 1-36. specif, pp. 2, 11.*
BD Biosciences. May 2012. Threshold and analysis of small particles on the BD Accuri C6 cytometer. Copyright 2012. Becton, Dickinson and Company, pp. 1-8. specif, p. 5.*
Flow Cytometry—A Basic Overview. Published Jun. 2018. Downloaded from the internet: <www.med.unc.edu/flowcytometry/files> pp. 1-7. specif, pp. 1, 2.*
Prewitt, J.M.S. Mathematical methods applied to image processing in medicine. In: Lecture Notes in Medical Informatics. Copyright 1981. Online Conferences, Ltd., Uxbridge, England. Eds. D.A.B. Lindberg and P.L. Reichertz. 8 pages.
BD Biosciences. Apr. 2000. Introduction to flow cytometry: a learning guide. Copyright 2000. Becton, Dickinson and Company. San Jose, CA. 54 pages.
Cibas, E.S. Cervical and Vaginal Cytology. In: Cytology: Diagnostic principles and clinical correlates. Third Edition. Copyright 2009. Saunders, an imprint of Elsevier, Inc. Eds.: Edmund S. Cibas and Barbara S. Ducatman. Philadelphia, PA pp. 39 pages.
Communication Pursuant to Article 94(3) EPC, Office Action, in Europe Application No. 14187908.0, dated Apr. 26, 2018, 6 pages.

* cited by examiner

*Primary Examiner* — Renee Claytor
*Assistant Examiner* — Sharon M. Papciak
(74) *Attorney, Agent, or Firm* — Crowell & Moring LLP

(57) ABSTRACT

Disclosed is a cell analysis method comprising: extracting target cells from a population of cells derived from an epithelial tissue on the basis of N/C ratio representing a relative size of a nucleus to a cytoplasm; classifying the target cells into at least a first group and a second group by difference of amount of DNA; and evaluating a pathology of the epithelial tissue by comparing a ratio of numbers of cells between the first and second groups with a threshold; wherein the threshold varies according to a proportion of the target cells in the population.

15 Claims, 15 Drawing Sheets

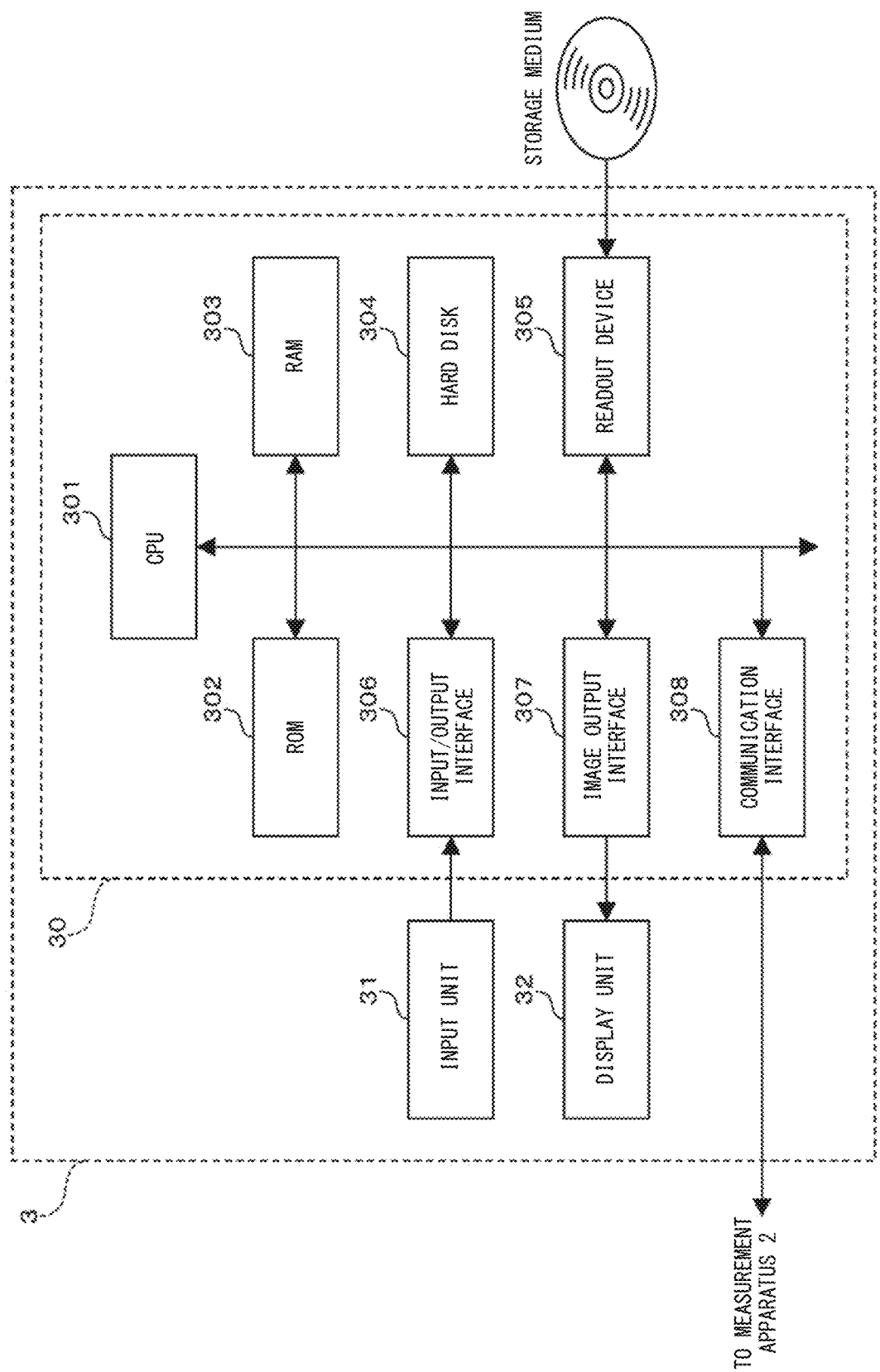
F I G. 5

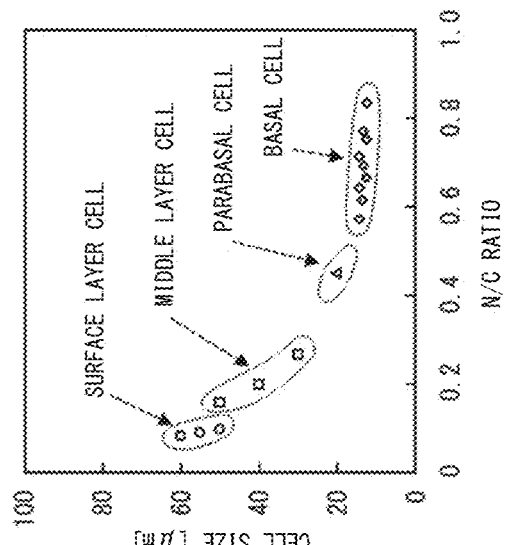
F I G. 7C
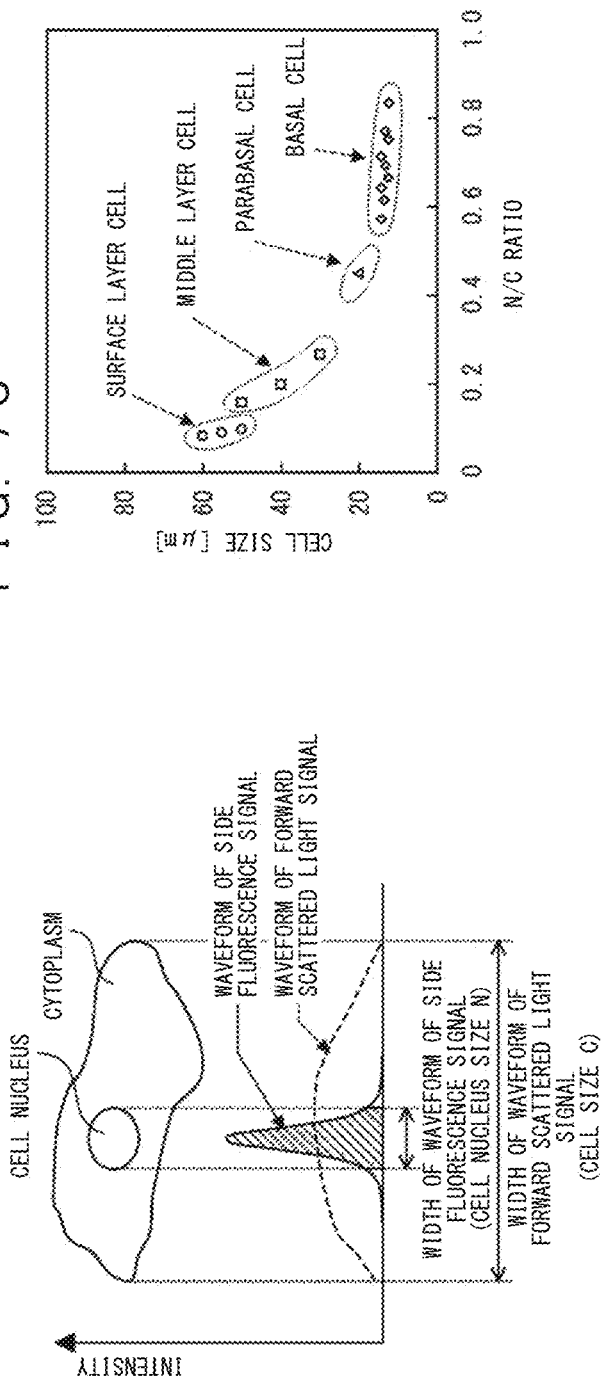
F I G. 7A
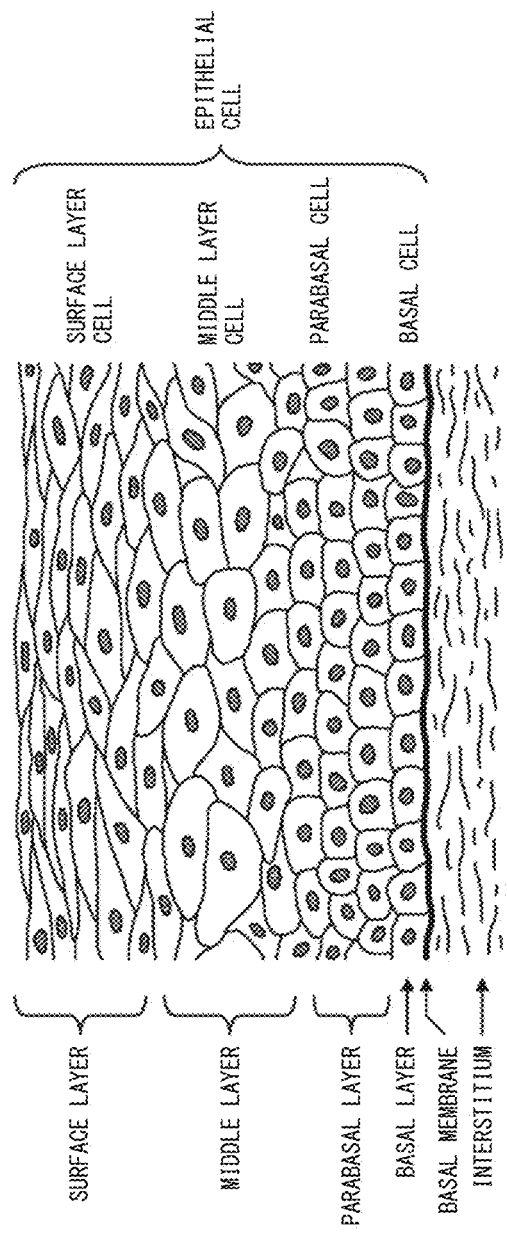
F I G. 7B

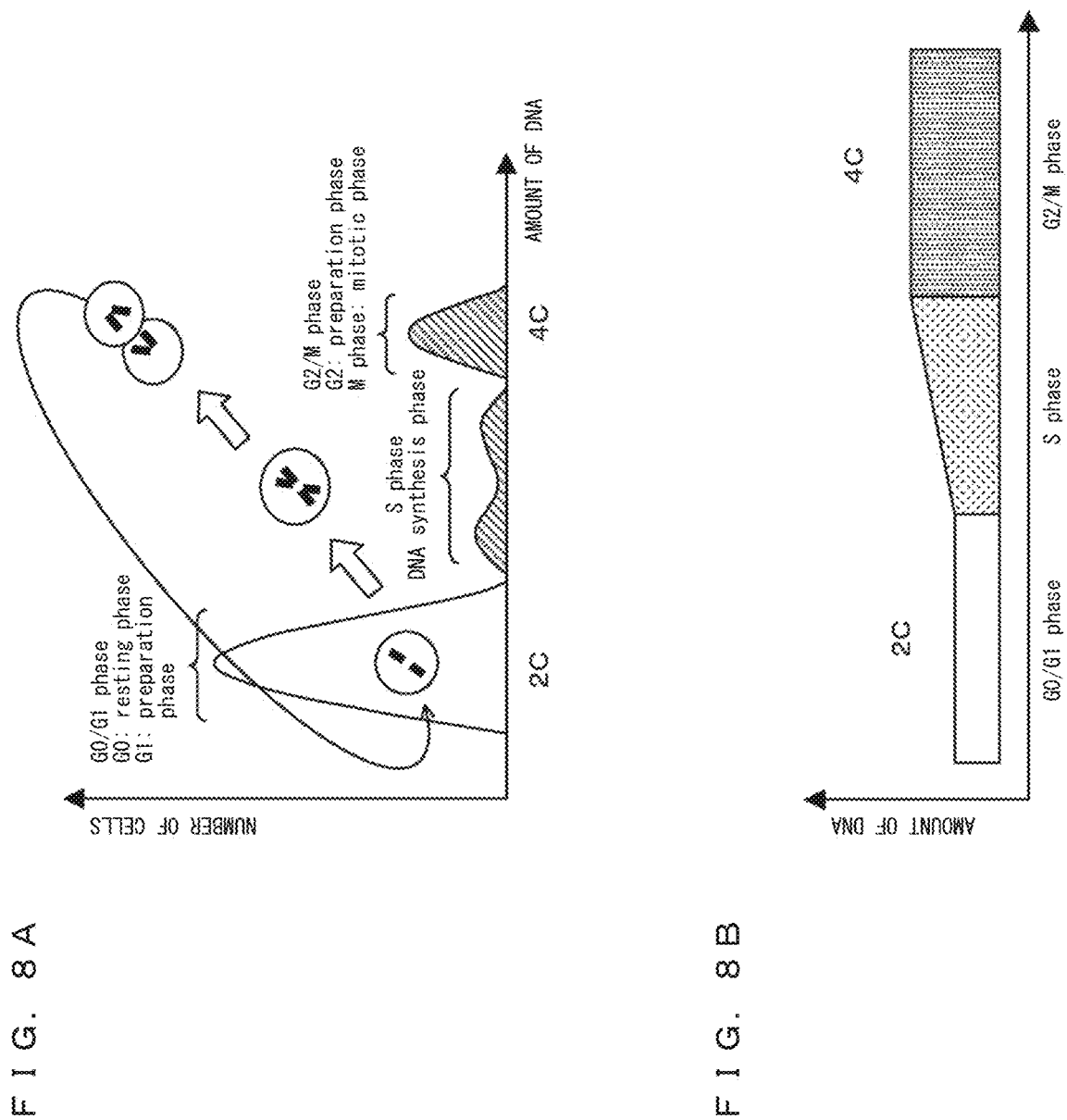

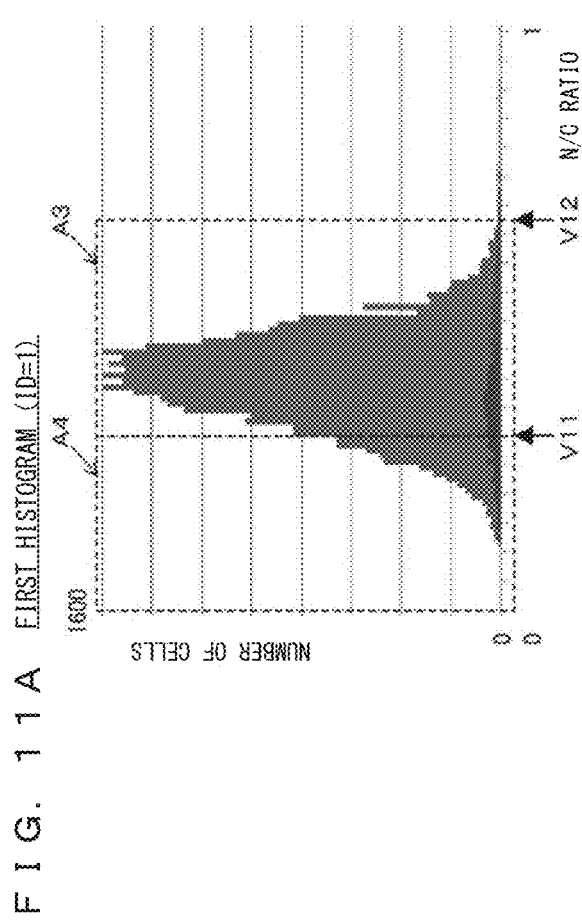

F I G. 13

CONDITION

| TOTAL NUMBER OF SAMPLES | 1020 |
|---|---|
| THE NUMBER OF POSITIVE SAMPLES | 54 |
| THE NUMBER OF NEGATIVE SAMPLES | 966 |

RESULT

| | VALUE OF THRESHOLD s4 | SENSITIVITY | SPECIFICITY |
|---|---|---|---|
| COMPARATIVE EXAMPLE | Vsh2 | 98% (53/54) | 73% (708/966) |
| PRESENT EMBODIMENT | When N1/N2 < s3, Vsh1 | 100% (7/7) | 80% (184/230) |
| | When N1/N2 ≥ s3, Vsh2 | 98% (46/47) | 78% (571/730) |
| | TOTAL | 98% (53/54) | 78% (755/966) |

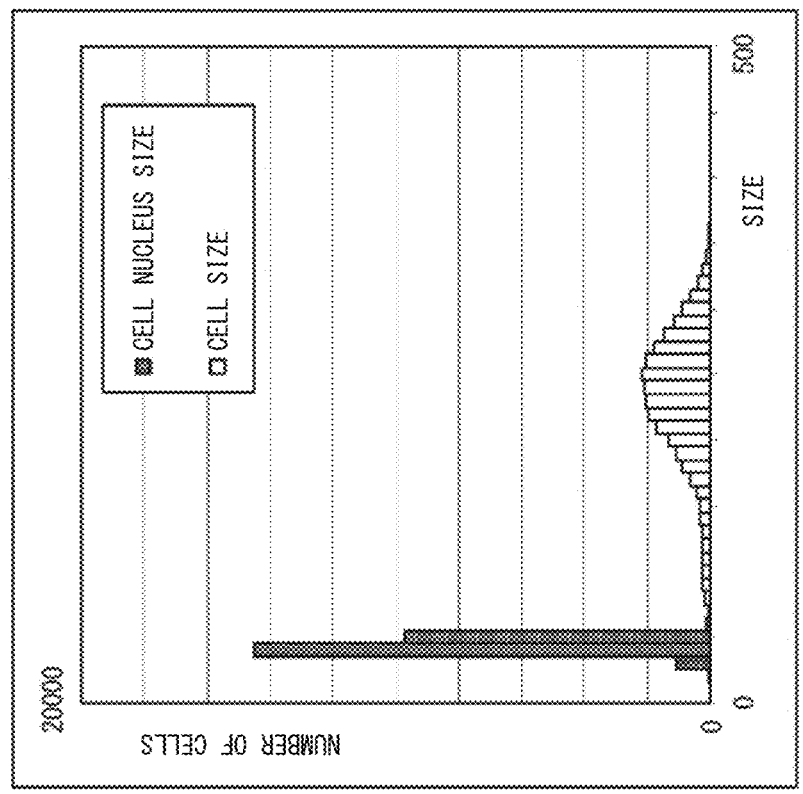
FIG. 14A  ID=1
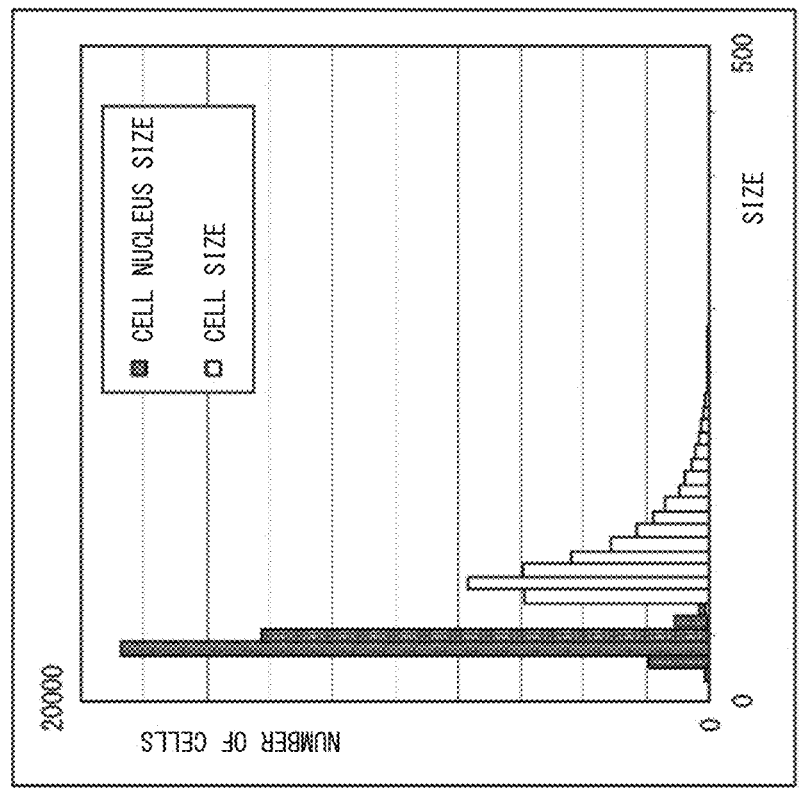
FIG. 14B  ID=2

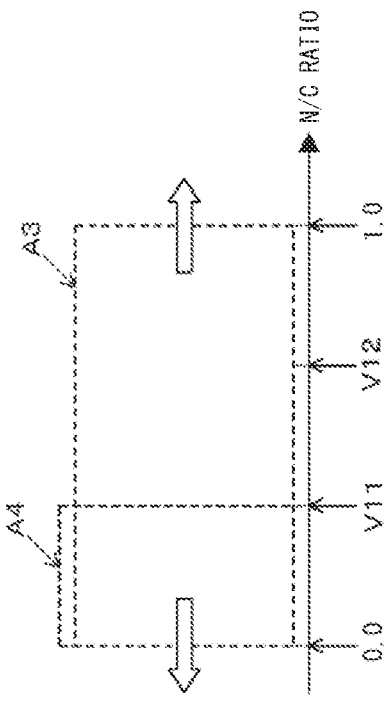
FIG. 15A  PATTERN 1
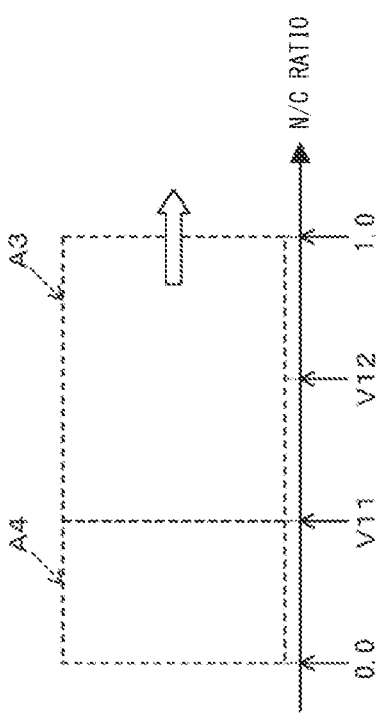
FIG. 15B  PATTERN 2
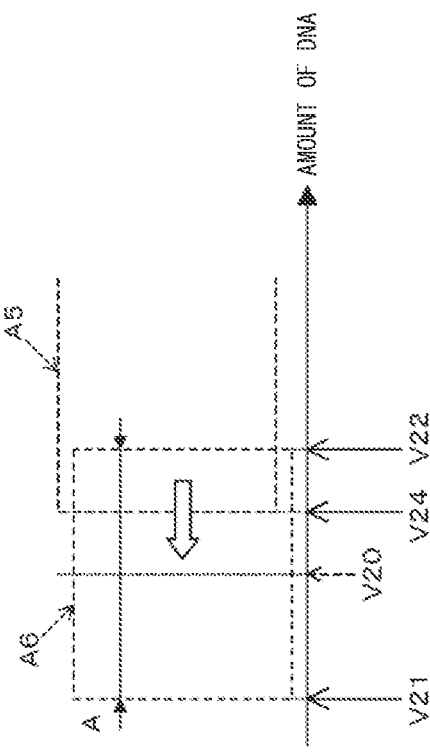
FIG. 15C  PATTERN 3
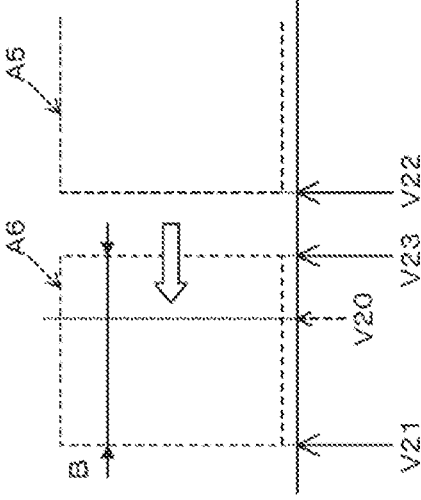
FIG. 15D  PATTERN 4

CELL ANALYSIS METHOD, CELL ANALYZER AND SAMPLE SCREENING METHOD

RELATED APPLICATIONS

This application is a continuation of U.S. application Ser. No. 14/508,522 filed on Oct. 7, 2014, which claims priority under 35 U.S.C. § 119 to Japanese Patent Application No. 2013-213930 filed on Oct. 11, 2013, the entire contents of which are hereby incorporated by reference.

FIELD OF THE INVENTION

The present invention relates to a cell analysis method, a cell analyzer and a sample screening method, preferably used in a medical test of clinical samples collected from subjects for screening cancer patient.

BACKGROUND OF THE INVENTION

There has been known an analyzer which automatically analyzes epithelial cells of a subject and which provides information regarding canceration of the cells (for example, see European patent application EP 2735872).

In the device of Japanese Laid-Open Patent Publication No. 2013-24768, a measurement specimen including epithelial cells collected from a subject is flowed in a flow cell, and the measurement specimen flowing in the flow cell is irradiated with light, whereby a scattered light signal and a fluorescence signal are obtained for each cell. Next, the waveforms of the scattered light signal and the fluorescence signal are analyzed, whereby canceration of cells are determined. Specifically, among epithelial cells included in the measurement specimen, with regard to cells on the basal layer side (target cells) which are to be analyzed, the number of cells in a range indicating a normal amount of DNA, and the number of cells in a range indicating an abnormal amount of DNA are obtained. Then, when the ratio between the numbers of the two types of cells is greater than or equal to a predetermined threshold, it is determined that canceration is suspected (positive).

However, how many target cells are contained in a sample is depending on skills of technician or the condition of site from which the epithelial tissue is collected. The proportion of target cells in a measurement specimen may be low in some cases and it may be high in other cases. Reliable evaluation of pathology is demanded regardless of theses fluctuant factors.

SUMMARY OF THE INVENTION

The scope of the present invention is defined solely by the appended claims, and is not affected to any degree by the statements within this summary.

A first aspect of the present invention is a cell analysis method comprising: extracting target cells from a population of cells derived from an epithelial tissue on the basis of N/C ratio representing a relative size of a nucleus to a cytoplasm; classifying the target cells into at least a first group and a second group by difference of amount of DNA; and evaluating a pathology of the epithelial tissue by comparing a ratio of numbers of cells between the first and second groups with a threshold; wherein the threshold varies according to a proportion of the target cells in the population.

A second aspect of the present invention is a cell analyzer comprising: a measurement apparatus comprising a cytometer; and a data processing device connected to the cytometer, and comprising a processor programmed to process data of cells obtained from the cytometer by: extracting target cells from a population of cells derived from an epithelial tissue on the basis of N/C ratio representing a relative size of a nucleus to a cytoplasm; determining a threshold according to a proportion of the target cells in the population; classifying the target cells into at least a first group and a second group by difference of amount of DNA; and evaluating a pathology of the epithelial tissue by comparing a ratio of numbers of cells between the first and second groups with the threshold determined.

A third aspect of the present invention is a sample screening method comprising: quantifying target cells in a measurement specimen prepared from a sample of epithelial tissue on the basis of N/C ratio representing a relative size of a nucleus to a cytoplasm; evaluating on the basis of quantity of the target cells whether the sample was appropriately collected from a subject; screening on the basis of amounts of DNA of the target cells the sample into groups of a cancer-suspected sample and other if the sample was appropriately collected; avoiding the screening if the collection of sample was inappropriate.

BRIEF DESCRIPTION OF THE DRAWINGS

FIG. 5 shows a configuration of a data processing device according to the embodiment;

FIG. 7A shows a diagram showing a forward scattered light signal and a fluorescence signal according to the embodiment;

FIG. 7B shows a schematic diagram showing an enlarged cross section of epithelial tissue of the uterine cervix;

FIG. 7C shows a diagram showing relationship between N/C ratio and cell size, according to the embodiment;

FIG. 8A shows a diagram showing relationship between the amount of DNA and the number of cells in a cell cycle;

FIG. 8B shows an amount of DNA changing in accordance with the cell cycle;

FIG. 11A shows a first histogram of a subject (ID=1) generated in the analysis process according to the embodiment;

FIG. 11B shows a first histogram of a subject (ID=2) generated in the analysis process according to the embodiment;

FIG. 11C shows a second histogram of the subject (ID=1) generated in the analysis process according to the embodiment;

FIG. 11D shows a second histogram of a subject (ID=2) generated in the analysis process according to the embodiment;

FIG. 13 shows determination results according to a comparative example and determination results according to the embodiment;

FIG. 14A show a histogram showing the number of cells in accordance with cell nucleus size and cell size for the subject (ID=1) according to a modification; and FIG. 14B show a histogram showing the number of cells in accordance with cell nucleus size and cell size for the subject (ID=2) according to a modification; and FIG. 15A to 15D show regions set in the first and second histograms according to a modification.

DETAILED DESCRIPTION OF THE PREFERRED EMBODIMENTS

The present embodiment is a cell analyzer which determines appropriateness of collection of cells from a subject and which obtains information regarding canceration of cells. Hereinafter, a cell analyzer 1 (hereafter referred to as analyzer 1) according to the present embodiment will be described with reference to the drawings.

The analyzer 1 flows, into a flow cell, a measurement specimen including cells collected from a subject. The analyzer 1 irradiates the measurement specimen flowing in the flow cell with laser light. The analyzer 1 detects forward scattered light, side scattered light, and fluorescence of cells in the measurement specimen and produces signals. The analyzer 1 analyzes the signals to determine whether cancerous cells or cells in the process of canceration (hereinafter, collectively referred to as "cancerous cells") are included. The analyzer 1 is used to screen cervical cancer by use of epithelial cells of the uterine cervix collected from a subject.

Figure 1:
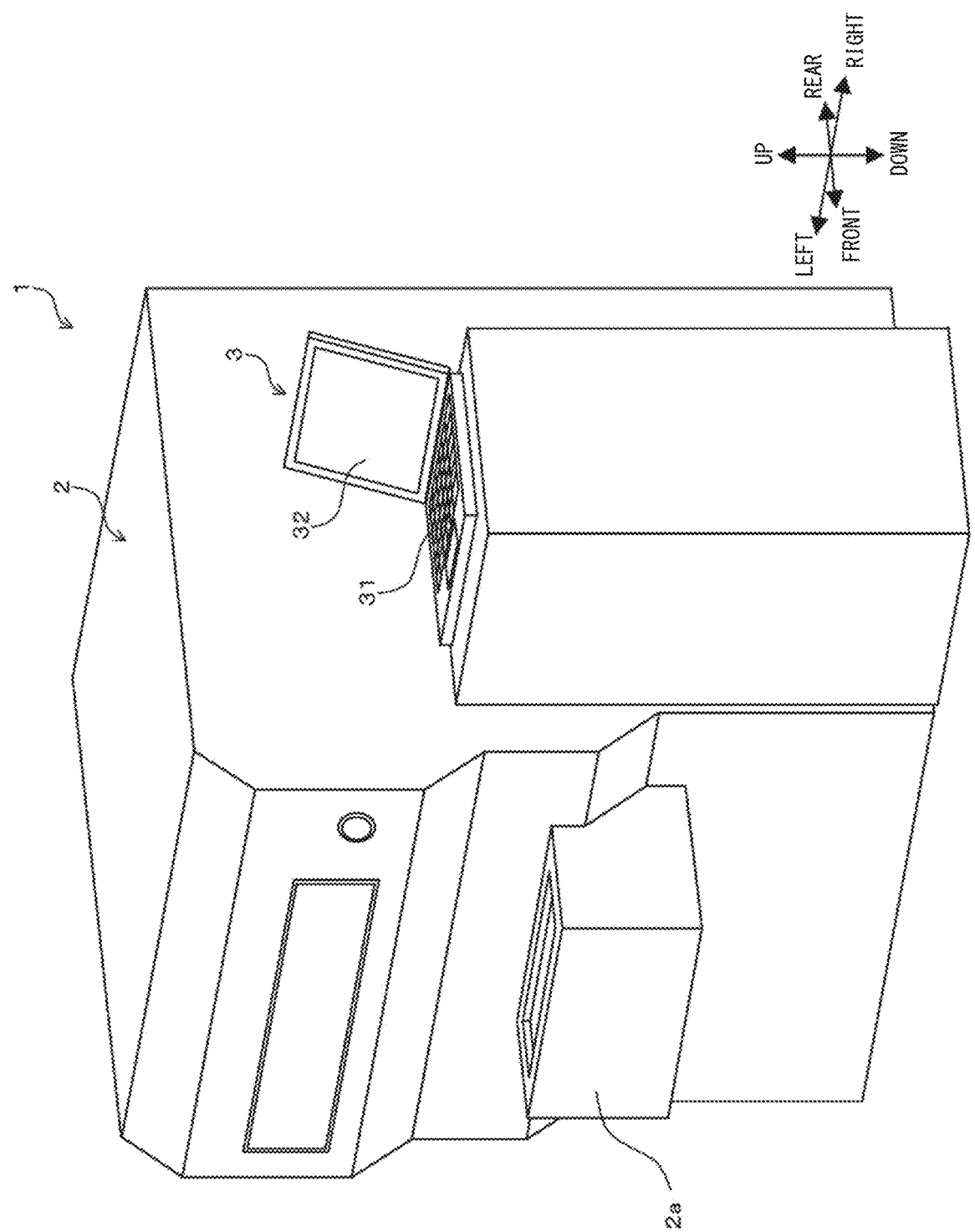
FIG. 1 is a schematic perspective view of an external structure of a canceration information providing apparatus according to an embodiment.

As shown in FIG. 1, the analyzer 1 includes: a measurement apparatus 2 which measures a measurement specimen including cells collected from a subject; and a data processing device 3 which is connected to the measurement apparatus 2 and which analyzes a measurement result and displays an analysis result. To the front face of the measurement apparatus 2, a sample setting unit 2a is provided for setting a plurality of specimen containers 4 (see FIG. 2) each containing a specimen, which contains cells collected from a subject and a preservative solution including methanol as a principal component. The data processing device 3 includes an input unit 31 and a display unit 32.

Figure 2:
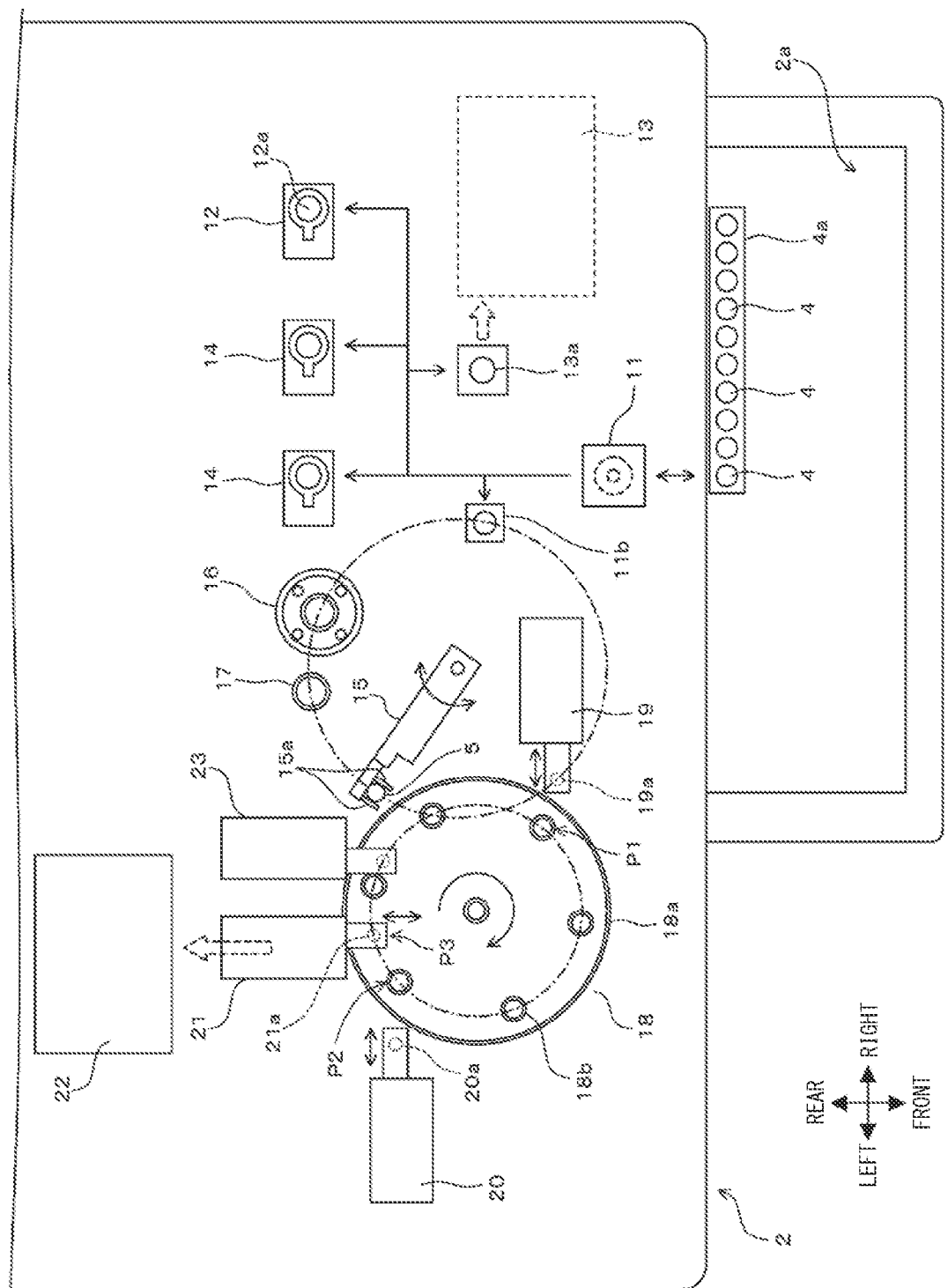
FIG. 2 is a schematic plan view showing a configuration of the inside of a measurement apparatus according to the embodiment.

As shown in FIG. 2, the sample setting unit 2a sequentially transports a rack 4a on which a plurality of specimen containers 4 are set, to an aspirating position at which the specimen is to be aspirated by a sample pipetting unit 11. The sample pipetting unit 11 transfers the specimen in each specimen container 4 to a specimen holding chamber 12a of a first dispersion unit 12. The sample pipetting unit 11 also transfers the specimen in the specimen holding chamber 12a to a specimen loading part 13a of a supplementary detection unit 13, and to a separation/substitution unit 14. The sample pipetting unit 11 also supplies a condensed solution obtained in the separation/substitution unit 14 to a measurement specimen container 5 located at a specimen relaying part 11b.

The first dispersion unit 12 performs a first dispersion process for dispersing aggregated cells included in the specimen supplied to the specimen holding chamber 12a. Specifically, the first dispersion process is a shearing force applying process in which a shearing force is applied to aggregated cells to mechanically disperse them. The supplementary detection unit 13 measures the concentration of the specimen before a main measurement is performed by a primary detection unit 22. The supplementary detection unit 13 employs a flow cytometer 40 (see FIG. 3A) having a substantially same configuration as that of the primary detection unit 22 described later.

The separation/substitution unit 14 receives the specimen having been subjected to the first dispersion process in the first dispersion unit 12. The separation/substitution unit 14 substitutes the preservative solution in the specimen with a diluent. The separation/substitution unit 14 also separates cells to be measured (epithelial cells and glandular cells of the uterine cervix) included in the specimen, from the other cells (red blood cells, white blood cell, bacteria, and the like) and impurities. The separation/substitution unit 14 also condenses cells to be measured included in the specimen, in order to obtain the number of cells necessary for measurement to be performed by the primary detection unit 22. Two separation/substitution units 14 are provided for performing the process efficiently.

A container transfer unit 15 grips a measurement specimen container 5 set in a reaction unit 18 by means of a scissors-shaped gripper 15a, to transfer the measurement specimen container 5 to each of the specimen relaying part 11b, a second dispersion unit 16, a liquid removing unit 17, and the reaction unit 18, along a predetermined circular path. The second dispersion unit 16 performs a second dispersion process, which is different from the first dispersion process, onto the specimen having been subjected to the first dispersion process in the first dispersion unit 12. Specifically, the second dispersion unit 16 is configured to apply ultrasonic vibration to the specimen having been subjected to the first dispersion process in the first dispersion unit 12 and condensed (the concentration of cells to be measured has been increased) in the separation/substitution unit 14. The second dispersion unit 16 disperses, into single cells, aggregated cells that are remaining even after the first dispersion process.

The liquid removing unit 17 removes (dries out) liquid attached to the external surface of the measurement specimen container 5 in the second dispersion process, by supplying airflow to the external surface of the measurement specimen container 5. The reaction unit 18 includes a round rotatable table 18a configured to be able to rotate. In an outer periphery portion of the rotatable table 18a, a plurality of holders 18b capable of holding a measurement specimen container 5 are provided. The reaction unit 18 heats the measurement specimen container 5 set in a holder 18b by the container transfer unit 15 to a predetermined temperature (about 37 Celsius degrees), to accelerate the reaction between the specimen in the measurement specimen container 5 and reagents added by a first reagent adding unit 19 and a second reagent adding unit 20.

The first reagent adding unit 19 and the second reagent adding unit 20 respectively add predetermined amounts of reagents from supply parts 19a and 20a into the measurement specimen container 5 transported to a position P1 and in turn to a position P2 by the rotatable table 18a. The reagent added by the first reagent adding unit 19 is an RNase used for RNA removing process. The reagent added by the second reagent adding unit 20 is a fluorescent stain used for DNA staining process to stain DNA of nucleus in cells. Through the RNA removing process, RNA freely contained in the measurement specimen and RNA in cells are resolved, whereby nonspecific stain of RNA can be avoided. The DNA staining process is performed by use of propidium iodide (PI), a fluorescence dye. Through the DNA staining process, the nucleus in each cell is selectively stained. Thus, fluorescence from the nucleus can be detected.

A specimen aspirating unit 21 aspirates, by means of a pipette 21a, the measurement specimen in the measurement specimen container 5 transported to a position P3 by the rotatable table 18a. The specimen aspirating unit 21 is also connected to a flow cell 43 (see FIG. 3A) of the primary detection unit 22, via a flow channel (not shown). The specimen aspirating unit 21 supplies the aspirated measurement specimen to the flow cell 43 of the primary detection unit 22. The primary detection unit 22 includes the flow cytometer 40 for detecting light (forward scattered light, side scattered light, fluorescence) from the measurement specimen. The primary detection unit 22 outputs signals based on the respective lights, to a circuit in the latter stage. The flow cytometer 40 will be described later with reference to FIG. 3A and FIG. 3B.

A container cleaning unit 23 discharges a cleaning liquid into the measurement specimen container 5 after the measurement specimen has been supplied to the primary detection unit 22 by the specimen aspirating unit 21. Thereby, the container cleaning unit 23 cleans the inside of the measurement specimen container 5. Thus, when the same measurement specimen container 5 is used in a measurement process thereafter, contamination to another specimen can be prevented.

Figure 3:
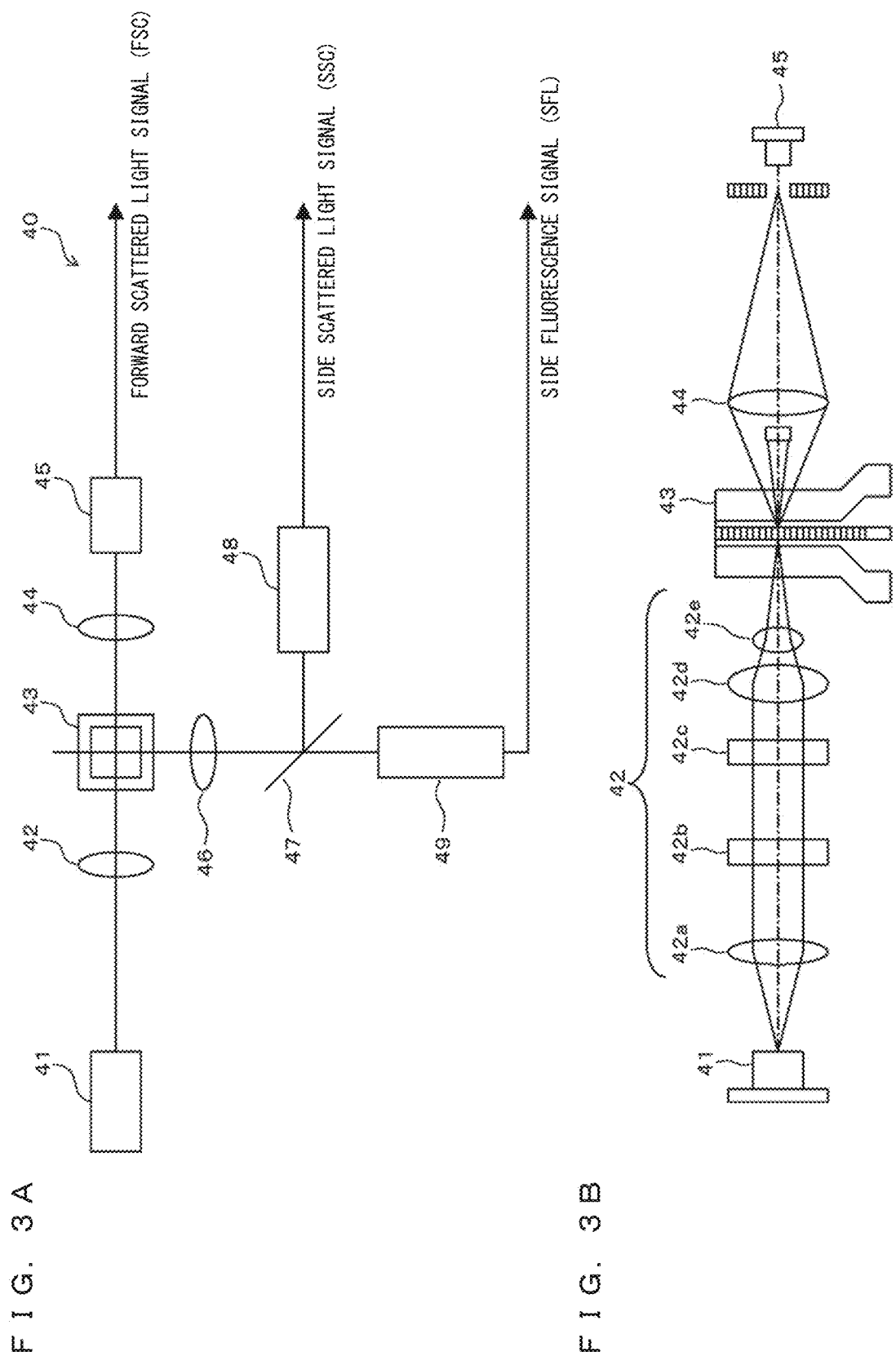
FIG. 3A shows a configuration of a flow cytometer in a plan view according to the embodiment.
FIG. 3B shows a configuration of a flow cytometer in a side view according to the embodiment.

FIG. 3A shows a configuration of the flow cytometer 40 of the primary detection unit 22. Laser light emitted from a light source 41 is condensed onto the measurement specimen flowing in the flow cell 43 by a lens system 42 including a plurality of lenses. As described above, to the flow cell 43, the specimen aspirated by the specimen aspirating unit 21 is supplied. As shown in FIG. 3B, the lens system 42 includes, from the light source 41 side, a collimator lens 42a, a cylindrical lens system including a plano-convex cylindrical lens 42b and a biconcave cylindrical lens 42c, and a condenser lens system including a condenser lens 42d and a condenser lens 42e, in this order.

A condenser lens 44 condenses forward scattered light from each cell in the measurement specimen onto a detector 45, a photodiode. A condenser lens 46 condenses side scattered light and fluorescence from each nucleus of cell to a dichroic mirror 47. The dichroic mirror 47 reflects side scattered light to a detector 48, a photo-multiplier tube. The dichroic mirror 47 passes fluorescence toward a detector 49, a photo-multiplier tube. In this manner, side scattered light is condensed onto the photomultiplier 48, and fluorescence is condensed onto the photomultiplier 49. These lights reflect characteristics of each cell and the nucleus thereof.

The detectors 45, 48 and 49 convert received lights into electric signals. The detector 45 outputs a forward scattered light signal (FSC) according to an intensity of forward scattered light. The detector 48 outputs a side scattered light signal (SSC) according to an intensity of side scattered light. The detector 49 outputs a fluorescence signal (SFL) according to an intensity of fluorescence. These output signals are amplified by preamplifiers, and in turn outputted to a signal processing unit 24 (see FIG. 4).

Figure 4:
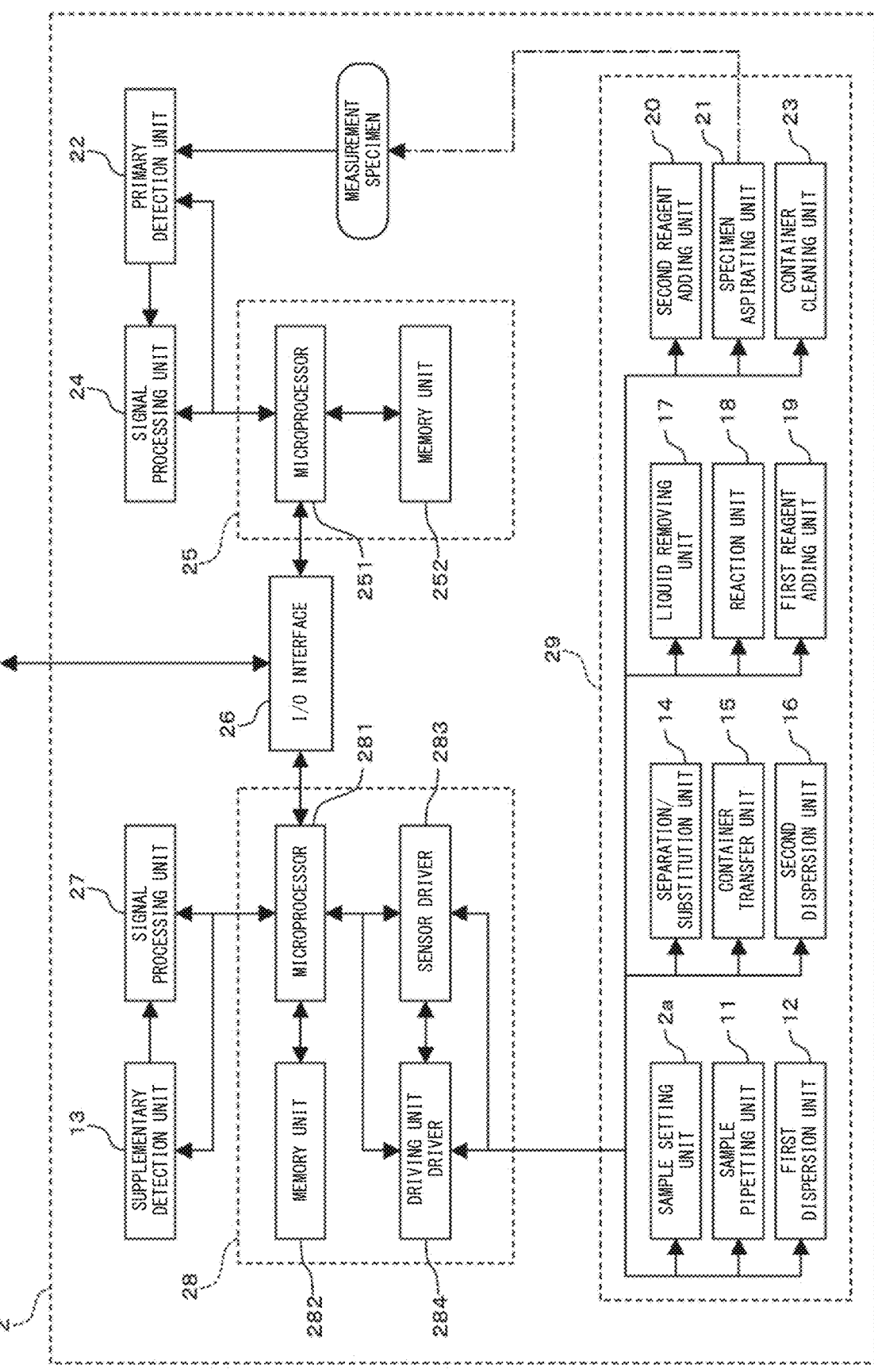
FIG. 4 shows a configuration of the measurement apparatus according to the embodiment.

As shown in FIG. 4, the measurement apparatus 2 includes the primary detection unit 22, the supplementary detection unit 13 and a preparation device unit 29 including various units for automatically preparing a measurement specimen as described above. The measurement apparatus 2 also includes the signal processing unit 24, a measurement control unit 25, an I/O interface 26, a signal processing unit 27, and a preparation control unit 28.

The primary detection unit 22 includes the flow cytometer 40 shown in FIG. 3A. The primary detection unit 22 outputs a forward scattered light signal (FSC), a side scattered light signal (SSC), and a fluorescence signal (SFL) of the measurement specimen. The signal processing unit 24 includes a signal processing circuit that performs signal processing on output signals from the primary detection unit 22. The signal processing unit 24 processes the respective signals, FSC, SSC, and SFL, outputted from the primary detection unit 22. The signal processing unit 24 outputs the resultant signals to the measurement control unit 25.

The measurement control unit 25 includes a microprocessor 251 and a memory unit 252. The microprocessor 251 is connected, via the I/O interface 26, to the data processing device 3 and a microprocessor 281 of the preparation control unit 28. Accordingly, the microprocessor 251 can transmit and receive various types of data to and from the data processing device 3 and the microprocessor 281 of the preparation control unit 28. The memory unit 252 includes, among others, a ROM and a RAM for storing control programs and data for the primary detection unit 22 and the like.

The respective signals, FSC, SSC, and SFL, processed in the signal processing unit 24 of the measurement apparatus 2 are transmitted by the microprocessor 251 via the I/O interface 26 to the data processing device 3.

Since the supplementary detection unit 13 employs the flow cytometer 40 having substantially the same configuration as that of the primary detection unit 22, the configuration of the supplementary detection unit 13 will be omitted. The supplementary detection unit 13 measures concentration of the specimen before the main measurement is performed by the primary detection unit 22. In the present embodiment, the supplementary detection unit 13 is configured to obtain forward scattered light signals (FSC). The supplementary detection unit 13 outputs signals for counting the number of cells having sizes corresponding to surface layer cells and middle layer cells based on forward scattered light signals. The signal processing unit 27 includes a signal processing circuit which performs signal processing on output signal from the supplementary detection unit 13. The signal processing unit 27 processes FSC. The signal processing unit 27 outputs the resultant signal to the preparation control unit 28.

The preparation control unit 28 includes the microprocessor 281, a memory unit 282, a sensor driver 283, and a driving unit driver 284. The microprocessor 281 is connected, via the I/O interface 26, to the microprocessor 251 of the measurement control unit 25. Accordingly, the microprocessor 281 can transmit and receive various types of data to and from the microprocessor 251 of the measurement control unit 25.

The memory unit 282 includes, among others, a ROM and a RAM for storing control programs and the like for controlling the supplementary detection unit 13, the preparation device unit 29, and the like. The preparation device unit 29 includes the sample setting unit 2a, the sample pipetting unit 11, the first dispersion unit 12, the separation/substitution unit 14, the container transfer unit 15, the second dispersion unit 16, the liquid removing unit 17, the reaction unit 18, the first reagent adding unit 19, the second reagent adding unit 20, the specimen aspirating unit 21, and the container cleaning unit 23, as shown in FIG. 2.

The microprocessor 281 is connected, via the sensor driver 283 or the driving unit driver 284, to sensors and driving motors of the components of the preparation device unit 29. Accordingly, the microprocessor 281 can control operation of driving motors by executing control programs based on detection signals from the sensors.

As shown in FIG. 5, the data processing device 3 is composed of a personal computer. The data processing device 3 includes a body 30, the input unit 31, and the display unit 32. The body 30 includes a CPU 301, a ROM 302, a RAM 303, a hard disk 304, a readout device 305, an input/output interface 306, an image output interface 307, and a communication interface 308.

The CPU 301 executes computer programs stored in the ROM 302 and computer programs loaded onto the RAM 303. The RAM 303 is used for reading out computer programs stored in the ROM 302 and the hard disk 304. The RAM 303 is also used as a work area for the CPU 301 when the CPU 301 executes these computer programs. Based on the respective signals, FSC, SSC, and SFL, received from the measurement apparatus 2, the CPU 301 obtains characteristic parameters such as the width of the waveform of the forward scattered light signal, the width of the waveform of the fluorescence signal, and the area of the waveform of the fluorescence signal. The CPU 301 performs analysis based on these characteristic parameters.

The hard disk 304 has installed therein various computer programs to be executed by the CPU 301 and data to be used in execution of the computer programs, such as an operating system and application programs. Specifically, the hard disk 304 has installed therein programs and the like for analyzing each measurement result transmitted from the measurement apparatus 2 and displaying on the display unit 32 based on the generated analysis result.

The readout device 305 is composed of a CD drive, a DVD drive, or the like. The readout device 305 can read out computer programs and data stored in a storage medium. To the input/output interface 306, the input unit 31 composed of a keyboard and the like is connected. Via the input unit 31, instructions and data are inputted to the data processing device 3. To the image output interface 307, the display unit 32 composed of a display and the like is connected. The image output interface 307 outputs an image signal corresponding to image data to the display unit 32. The display unit 32 displays an image based on the inputted image signal. Through the communication interface 308, transmission/reception of data to/from the measurement apparatus 2 can be performed.

Figure 6:
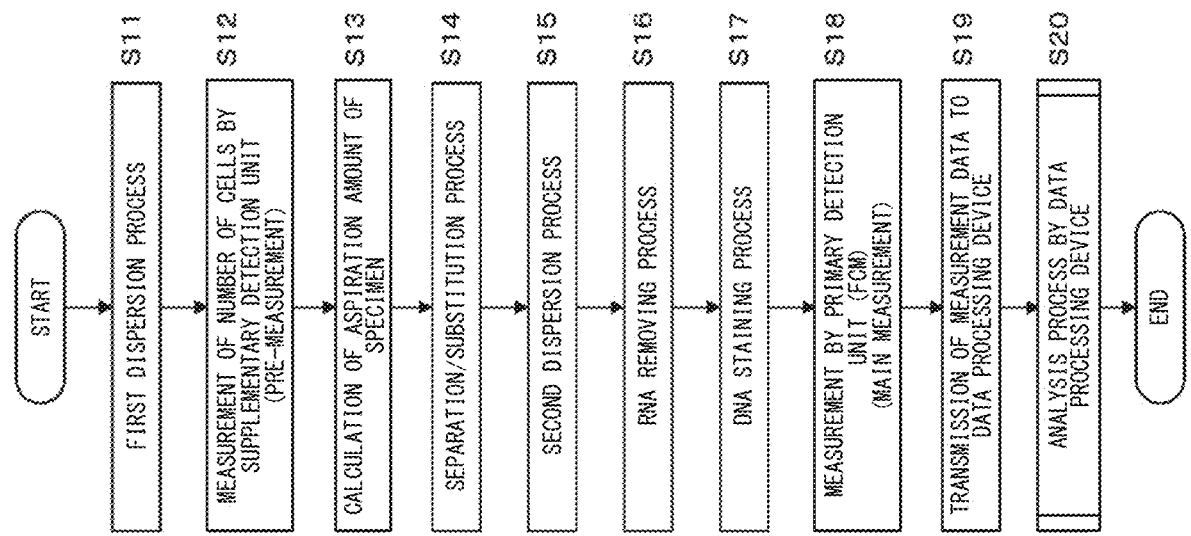
FIG. 6 is a flow chart showing analysis operation performed by the canceration information providing apparatus according to the embodiment.

FIG. 6 is a flow chart showing operation performed in the primary detection unit 22 and the signal processing unit 24 of the measurement apparatus 2. Control of the operation is performed by the microprocessor 251 of the measurement control unit 25. Control of operation of the supplementary detection unit 13, the signal processing unit 27, and the preparation device unit 29 of the measurement apparatus 2 is performed by the microprocessor 281 of the preparation control unit 28. Control of the data processing device 3 is performed by the CPU 301.

Prior to analysis by the analyzer 1, a specimen container 4 containing a biological specimen and the preservative solution is set in the sample setting unit 2a (see FIG. 2) by an operator. Then, measurement by the analyzer 1 is started. Upon start of the measurement, the specimen in the specimen container 4 set in the sample setting unit 2a is aspirated by the sample pipetting unit 11, to be supplied into the specimen holding chamber 12a. Then, a dispersion process (the first dispersion process) of aggregated cells in the specimen is performed by the first dispersion unit 12 (S11).

Upon completion of the first dispersion process, the specimen is supplied by the sample pipetting unit 11 into the specimen loading part 13a of the supplementary detection unit 13. Then, the specimen having been subjected to dispersion is flowed by a predetermined amount into the flow cell of the supplementary detection unit 13. In the supplementary detection unit 13, the number of normal cells that are present on the surface layer side relative to basal cells in epithelial tissue included in the specimen is detected (pre-measurement) by flow cytometry (S12). In the present embodiment, as the number of normal cells above, the number of surface layer cells and middle layer cells is detected. Based on the number of surface layer cells and middle layer cells obtained in the pre-measurement, and the volume of the specimen supplied to the supplementary detection unit 13, the concentration of this specimen is calculated.

Subsequently, based on the calculated concentration, an aspiration amount of the specimen for preparing a measurement specimen to be used in the main measurement is determined by the microprocessor 281 (S13). That is, based on the concentration (the number of cells per unit volume) of the specimen used in the pre-measurement and the number of surface layer cells and middle layer cells necessary for detection of cancer cells in the main measurement being the targeted measurement, the liquid amount of the specimen necessary for performing the main measurement is calculated such that the number of surface layer cells and middle layer cells is secured. In the present embodiment, it is assumed that the number of surface layer cells and middle layer cells to be supplied to the flow cell 43 of the primary detection unit 22 is about 20,000. In this case, it is necessary that about 100,000 surface layer cells and middle layer cells are included in the specimen to be supplied to the separation/substitution unit 14. Thus, the liquid amount of the specimen is calculated in S13 such that about 100,000 surface layer cells and middle layer cells are supplied to the separation/substitution unit 14.

In the number of surface layer cells and middle layer cells obtained in the pre-measurement, single cells and aggregated cells of epithelial cells are both included, and in addition, white blood cells and the like other than epithelial cells are also included. That is, even in a case where 100,000 surface layer cells and middle layer cells are supplied to the separation/substitution unit 14, actually, the number of cells to be supplied to the flow cell 43 of the primary detection unit 22 is more or less than 20,000 being the target number. However, based on the number of cells obtained in the pre-measurement, it becomes possible to keep the number of cells necessary for the main measurement constant to some extent.

Next, the specimen after the first dispersion process is aspirated by the calculated liquid amount from the specimen holding chamber 12a of the first dispersion unit 12. The aspirated specimen is supplied to the separation/substitution unit 14. Then, in the separation/substitution unit 14, a separation/substitution process is performed (S14). Next, the specimen aspirated by the sample pipetting unit 11 from the separation/substitution unit 14 is supplied to a measurement specimen container 5 located at the specimen relaying part 11b. This measurement specimen container 5 is transferred to the second dispersion unit 16 by the container transfer unit 15. Then, a dispersion process (the second dispersion process) of aggregated cells in the specimen is performed in the second dispersion unit 16 (S15).

Next, into the measurement specimen container 5 containing the specimen after the second dispersion process, a reagent (RNase) is added by the first reagent adding unit 19. This measurement specimen container 5 is heated by the reaction unit 18, and the RNA removing process is performed on the cells to be measured in the measurement specimen container 5 (S16). Next, into the measurement specimen container 5 containing the specimen after the RNA removing process, a reagent (stain solution) is added by the second reagent adding unit 20. This measurement specimen container 5 is heated by the reaction unit 18, and the DNA staining process is performed on the cells to be measured in the measurement specimen container 5 (S17). In the present embodiment, through the pre-measurement, a significant number of cells necessary for the main measurement is kept constant to some extent. Thus, the degree of staining of cells is less likely to vary among measurements.

Next, the measurement specimen having been subjected to the DNA staining process is aspirated by the specimen aspirating unit 21. The aspirated measurement specimen is sent to the flow cell 43 (see FIG. 3A) of the primary detection unit 22, and the main measurement is performed on cells in the measurement specimen (S18). After the main measurement, measurement data obtained from individual particles is transmitted from the measurement control unit 25 of the measurement apparatus 2 to the data processing device 3 (S19). Specifically, the forward scattered light signal (FSC), the side scattered light signal (SSC), and the fluorescence signal (SFL) obtained for each cell in the measurement specimen are transmitted to the data processing device 3. The CPU 301 of the data processing device 3 is always checking whether measurement data has been received from the measurement apparatus 2. Upon receiving measurement data from the measurement apparatus 2, the CPU 301 performs an analysis process based on the received measurement data (S20). Details of the analysis process in S20 will be described later with reference to FIG. 9.

Next, a procedure of obtaining canceration information in the present embodiment will be described.

FIG. 7A illustrates a forward scattered light signal (FSC) and a fluorescence signal (SFL) obtained in the main measurement (S18 in FIG. 6). In FIG. 7A, a schematic view of a cell including a cell nucleus, and the waveform of the forward scattered light signal and the waveform of the fluorescence signal obtained from the cell are shown. The vertical axis represents level of signal, or intensity of light. The width of the waveform of the forward scattered light signal represents a width of the cell (referred to as cell size C). The width of the waveform of the fluorescence signal represents a width of the cell nucleus (cell nucleus size N). As shown with diagonal lines, the area of the region defined by the waveform of the fluorescence signal and baseline represents the amount of DNA of the cell.

FIG. 7B is a schematic diagram showing an enlarged cross section of epithelial tissue of the uterine cervix. As shown in FIG. 7B, the uterine cervix has, in order from the basal membrane side, a basal layer formed by basal cells, a parabasal layer formed by parabasal cells, a middle layer formed by middle layer cells, and a surface layer formed by surface layer cells. According to getting mature, basal cells near the basal membrane become parabasal cells, parabasal cells become middle layer cells, and middle layer cells become surface layer cells.

Among these epithelial cells, basal cells pertains to canceration of uterine cervix. In the process of becoming a cancer, basal cells acquire atypical formation and become atypical cells. The atypical cells acquire proliferative capacity, and occupy from the basal layer side to the surface layer side. Thus, in the initial stage of cancer progress of uterine cervix, many cancerous cells exist in the basal layer, the parabasal layer, and the middle layer. In contrast, in the initial stage, cancerous cells are extremely few in the surface layer side.

The size of a cell gradually gets smaller from the surface layer side toward the basal membrane side, compared with the size of the cell nucleus. Therefore, the ratio of the cell nucleus size (N) relative to the cell size (C) (hereinafter, referred to as "N/C ratio") gradually becomes larger from the surface layer side toward the basal membrane side. Thus, the N/C ratio and the cell size C have relationship as shown in FIG. 7C. By extracting cells having a large N/C ratio, parabasal cells and basal cells can be extracted as analysis target.

Epithelial cells of the uterine cervix collectable from a subject are parabasal cells, middle layer cells, and surface layer cells. Precancerous change appears early on the basal cell side. Therefore, if parabasal cells are appropriately collected from a subject, precancerous change in the initial stage of uterine cervix cancer can be appropriately detected in determination of canceration described later. In the present embodiment, before the determination of canceration, whether parabasal cells have been appropriately collected is determined by use of the N/C ratio.

FIG. 8A shows relationship between the amount of DNA in a cell cycle and the number of cells. As shown in FIG. 8A, a cell goes through events such as DNA replication, distribution of chromosomes, nuclear division, and cytoplasmic division according to a cell cycle, to become two cells, then returning to the starting point. The cell cycle can be divided into four phases: G1 phase (period for preparation to enter S phase), S phase (DNA synthesis phase), G2 phase (period for preparation to enter M phase), and M phase (mitotic phase) in addition to G0 phase (resting phase) when proliferation of the cell is resting. Cell is in one of the stages of the five phases.

When a cell proliferates according to the cell cycle, chromosomes of the nucleus in the cell also increase. By measuring the amount of DNA of the cell, what state of the cell cycle the cell is in can be estimated. In the case of a normal cell, as shown in FIG. 8B, the amount of DNA in the G0/G1 phase is 2C as almost constant value. In the subsequent S phase, the amount of DNA gradually increases. Then, in the G2 phase, the amount of DNA becomes 4C as a constant value. This value is maintained also in the M phase. Here, C represents the genomic DNA content per haploid. That is, 2C represents an amount of DNA two times of the genomic DNA content per haploid. 4C represents an amount of DNA four times of the genomic DNA content per haploid. The amount of DNA of a normal cell in the G0 phase or the G1 phase of the cell cycle is 2C. With respect to normal cells, when a histogram of the amount of DNA is created, a histogram as shown in FIG. 8A is obtained. A hill having the highest peak corresponds to cells in the G0/G1 phase in which the amount of DNA is the least. A hill having the second highest peak corresponds to cells in the G2/M phase in which the amount of DNA is the largest. Hills between the above two hills corresponds to cells in the S phase.

In the case of normal cells, the number of cells in the state of the S phase and the G2/M phase is extremely small compared with the number of cells in the G0/G1 phase. However, in the case of cancerous cells, the number of cells in the state of the S phase and the G2/M phase becomes large compared with that of normal cells. Moreover, in the case of cancerous cells, since the number of chromosomes of cells also increases, the amount of DNA also increases.

Thus, in the present embodiment, a determination method based on the N/C ratio and the amount of DNA is used to determine a canceration.

Specifically, by extracting cells having a large N/C ratio (hereinafter, referred to as "target cells"), parabasal cells easy to be cancer in early stage are extracted. Subsequently, in the extracted cells, cells having a large amount of DNA and thus having a high possibility of being cancerous cells (referred to as first cells) and cells having a small amount of DNA and thus having a low possibility of being cancerous cells (referred to as second cells) are respectively quantified. The number of first cells increases while the number of second cells decreases in process of canceration of tissue advances. Therefore, the ratio of the number of first cells relative to the number of second cells (hereinafter, referred to as "canceration ratio") greatly differs depending on canceration of cells. Therefore, by determining whether the canceration ratio is greater than or equal to a predetermined threshold, canceration can be determined.

The proportion of target cells included in a measurement specimen may vary depending on skill of a technician or an operator, and/or on condition of part from which the tissue is collected. Even if tissues are collected from subjects in same pathological condition, there may be a case where one contains much of cells of large N/C ratio while other contains few. Therefore it is not preferable to determine a canceration by comparing the canceration ratio with fixed predetermined.

In the present embodiment, a threshold for evaluating the canceration ratio is adjusted in accordance with the ratio of target cells included in a measurement specimen. Accordingly, even when the ratio of target cells included in the measurement specimen has varied, suitable threshold is applied to evaluate the canceration ratio. Hereinafter, a process including setting of such a threshold and determination of canceration will be described.

Figure 9:
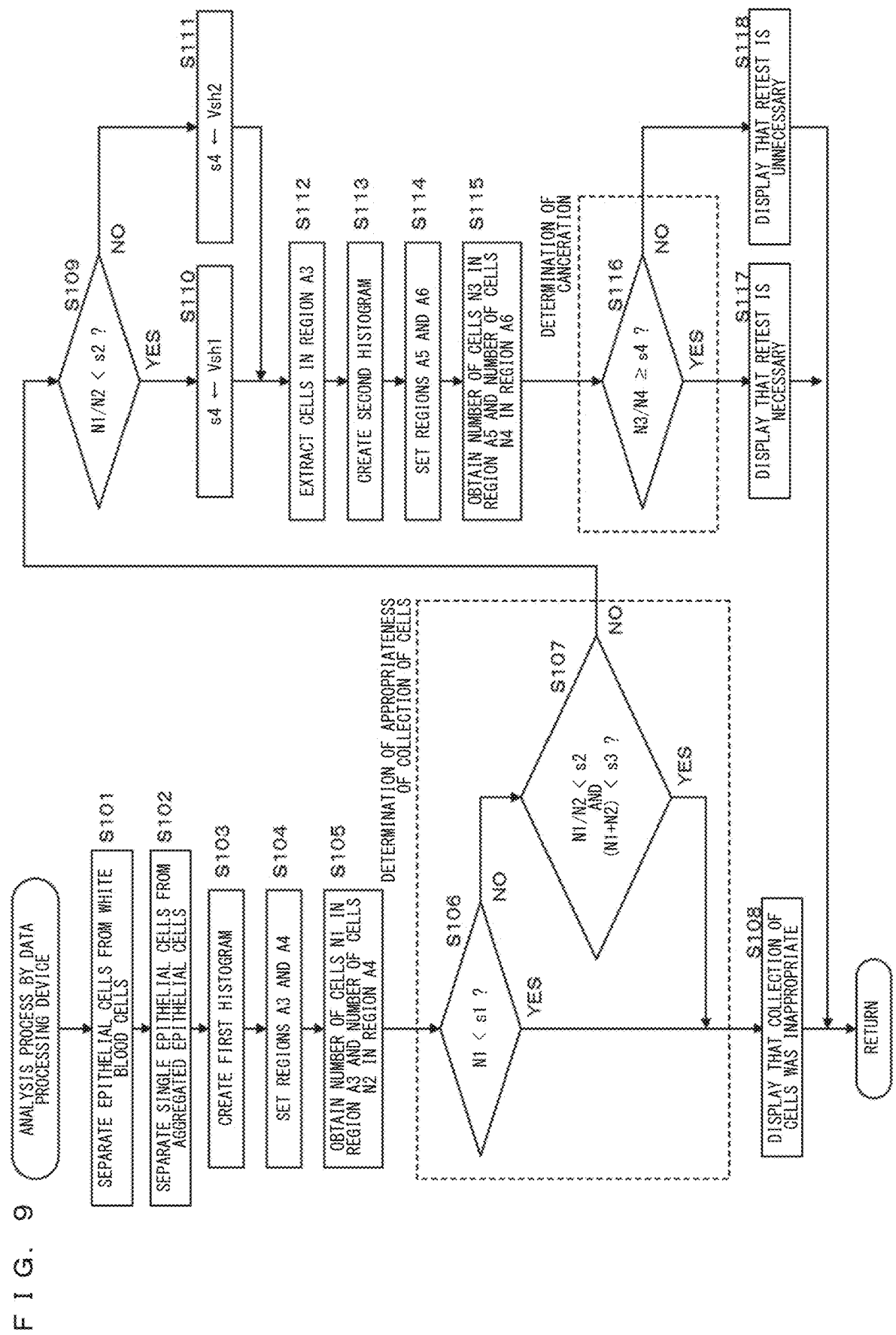
FIG. 9 is a flow chart showing an analysis process performed in the data processing device according to the embodiment.

FIG. 9 is a flow chart showing an analysis process performed in the data processing device 3.

Figure 10B:
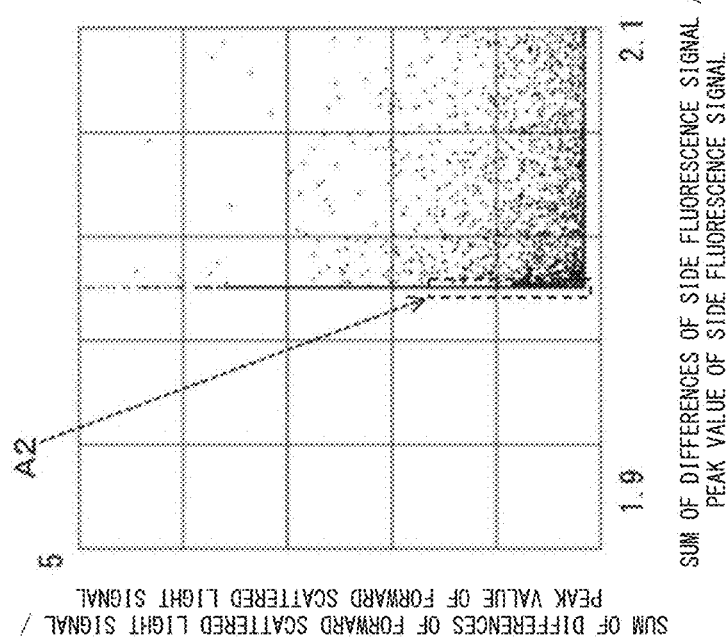
FIG. 10B shows a scattergram generated in S102 of the analysis process according to the embodiment.
Figure 10A:
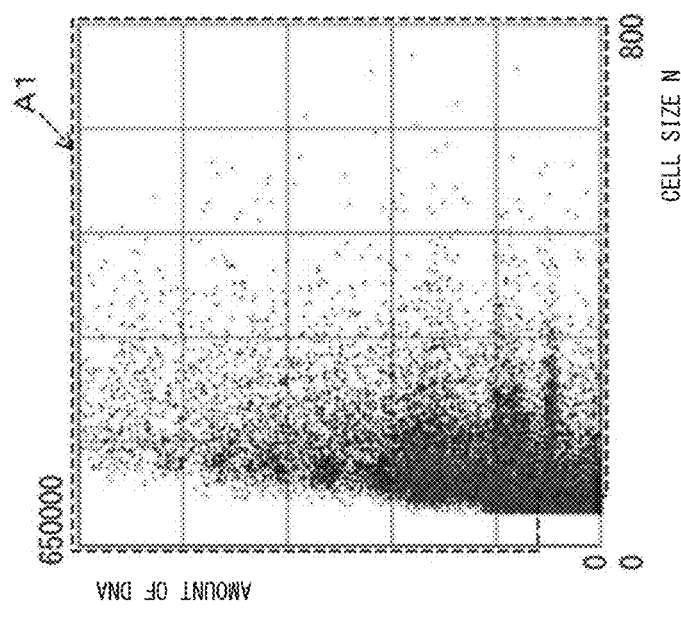
FIG. 10A shows a scattergram generated in S101 of the analysis process according to the embodiment.

Upon receiving measurement data from the measurement apparatus 2, the CPU 301 of the data processing device 3 classifies the particles into white blood cells and epithelial cells based on the received measurement data (S101). Specifically, as shown in FIG. 10A, each particle included in the measurement data is plotted on a scattergram having two axes of cell size N (width of waveform of FSC) and the amount of DNA (area of waveform of SFL). Subsequently, a region A1 is defined in this scattergram. The region A1 corresponds to epithelial cells. The region other than the region A1 is a region corresponding to white blood cells. Then, epithelial cells included in the region A1 are extracted.

In order to make explanation easy extraction of epithelial cells in the measurement date is carried out by plotting particles on the scattergram and extracting plots contained in defined region, however the scattergram and the region A1 may not be necessarily created to extract desired cells. Extraction of desired cells may be performed by filtering cells whose signal belongs to a specific numerical value range. Similarly, a scattergram (FIG. 10B) and a region A2, a first histogram and regions A3 and A4, and a second histogram and regions A5 and A6 described later and may not necessarily created for extracting desired cells. Counting the number of and extraction of cells included in the regions A2 to A6 may be performed by through data processing.

The CPU 301 classifies epithelial cells extracted in S101 into single epithelial cells and aggregated epithelial cells (S102). Specifically, as shown in FIG. 10B, the epithelial cells extracted in S101 are plotted on a scattergram having two axes of "sum of differences of fluorescence signal/peak value of fluorescence signal", and "sum of differences of forward scattered light signal/peak value of forward scattered light signal". Region A2 is set in this scattergram. The region A2 corresponds to single epithelial cells. Then, single epithelial cells included in the region A2 are extracted. Removal of aggregated epithelial cells are performed to prevent lowering of accuracy in determination of appropriateness of collection of cells (S106, S107) and determination of canceration (S116) described later.

The CPU 301 creates first histogram (S103) as shown in FIGS. 11A and 11B depicting the number of cells relative to the N/C ratio, with regard to the single epithelial cells extracted in S102. FIG. 11A is the first histogram created based on a sample (ID=1) collected from a healthy subject of age 61. FIG. 11B is the first histogram created based on a sample (ID=2) collected from a healthy subject of age 53. It is seen that even between subjects in the same pathological condition, the number of cells having a large N/C ratio is large in the case of FIG. 11A, and the number of cells having a large N/C ratio is small in the case of FIG. 11B.

The CPU 301 sets region A3 which defines $V11 \leq N/C$ ratio$\leq V12$ and region A4 which defines N/C ratio$<V11$ in the first histogram (S104). The CPU 301 obtains the number of cells N1 included in the region A3 and the number of cells N2 included in the region A4 (S105).

V11 the boundary between the regions A3 and A4 is a threshold that separates middle layer cells from parabasal cells. V11 is set as appropriate from the viewpoint of sensitivity and specificity. In a preferred embodiment, V11 is set in a range of 0.2 to 0.4. V12 the right end of the region A3 is a threshold that separates parabasal cells from basal cells and unknown cells. V12 is set as appropriate from the viewpoint of sensitivity and specificity. In a preferred embodiment, V12 is set in a range of 0.6 to 1. In the present embodiment, the left end of the region A4 is set so as to include all cells in the left direction.

The CPU 301 performs determination of appropriateness of collection of cells (S106, S107) based on the number of cells N1 and the number of cells N2 obtained in S105.

In S106, the CPU 301 determines whether the number of cells N1 is smaller than a threshold s1. The threshold s1 is a threshold for determining appropriateness of collection of parabasal cells. The threshold s1 is set as appropriate from the viewpoint of sensitivity and specificity. In a preferred embodiment, the threshold s1 is set in a range not smaller than 50 but not greater than 1000.

Figure 12A:
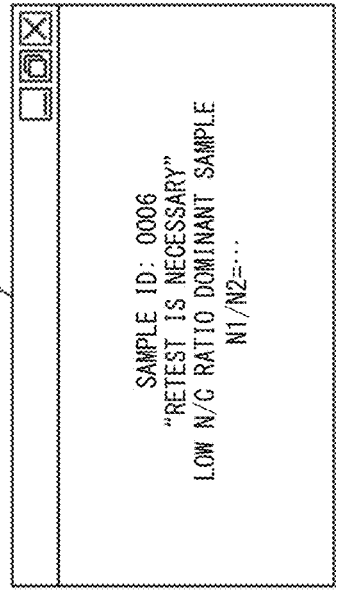
FIG. 12A to 12E show dialogue boxes to be displayed on a display unit according to the embodiment.

When the number of cells N1 is not large enough, there is a possibility that collection of parabasal cells was inappropriate. Therefore, when the number of cells N1 is smaller than the threshold s1 (S106: YES), the CPU 301 causes the display unit 32 to display a dialogue box D1 indicating that collection of parabasal cells was inappropriate (see FIG. 12A) (S108). In this case, the CPU 301 ends the process with skipping determination of canceration (S116) and output of canceration information (S117, S118) in the latter stage.

On the other hand, when the number of cells N1 is greater than or equal to the threshold s1 (S106: NO), determination in S107 is further performed. In S107, CPU 301 determines whether the ratio N1/N2 is smaller than a threshold s2, and the sum N1+N2 is smaller than a threshold s3. The threshold s2 is a threshold for determining whether the number of parabasal cells is greater than the number of cells on the surface layer side. The threshold s2 is set as appropriate from the viewpoint of sensitivity and specificity. In a preferred embodiment, the threshold s2 is set in a range not smaller than 0.1 but not greater than 0.4. The threshold s3 is a threshold for determining whether the absolute number of single epithelial cells is large enough. The threshold s3 is set as appropriate from the viewpoint of sensitivity and specificity.

When the ratio N1/N2 is smaller than the threshold s2, and the sum N1+N2 is smaller than the threshold s3 (S107: YES), the CPU 301 causes the display unit 32 to display the dialogue box D1 indicating that collection of parabasal cells was inappropriate (S108). Also in this case, the CPU 301 ends the process with skipping determination of canceration (S116) and output of canceration information (S117, S118) in the latter stage. When S107 is NO, collection of cells is determined as appropriate, and the process is advanced to the latter stage.

The CPU 301 determines whether the ratio N1/N2 is smaller than the threshold s2 (S109). When the ratio N1/N2 is smaller than the threshold s2 (S109: YES), the CPU 301 sets Vsh1 as a threshold s4 (S110). When the ratio N1/N2 is greater than or equal to the threshold s2 (S109: NO), the CPU 301 sets as the threshold s4 Vsh2 which is smaller than Vsh1 (S111). The threshold s4 is a value to be used in determination of canceration (S116) in the latter stage.

As described above, the number of target cells having a large N/C ratio varies depending on the sample. In the present embodiment, relative amount of target cells is calculated as the ratio N1/N2. Based on the relative amount, the threshold s4 to be used in determination of canceration is set to either Vsh1 or Vsh2.

According to the verification by the inventors, the following has been confirmed: when the ratio N1/N2 is high as in FIG. 11A, a canceration ratio N3/N4 determined in the step of determination of canceration (S116) described later tends to be low; and when the ratio N1/N2 is low as in FIG. 11B, the canceration ratio N3/N4 tends to be high. Thus, by adjusting the threshold s4 in accordance with the ratio N1/N2, accuracy of determination of canceration (S116) in the latter stage can be increased.

The CPU 301 extracts the target cells included in the region A3 of the first histogram (S112). With regard to the extracted cells, the CPU 301 creates the second histogram (DNA ploidy) showing the number of cells in accordance with the amount of DNA as shown in FIGS. 11C and 11D (S113). FIG. 11C is the second histogram created based on the cells included in the region A3 of the first histogram (ID=1) shown in FIG. 11A. FIG. 11D is the second histogram created based on the cells included in the region A3 of the first histogram (ID=2) shown in FIG. 11B.

The CPU 301 sets, in the second histogram, a region A5 which defines the amount of DNA≥V22 and a region A6 which defines V21≤amount of DNA≤V22 (S114). Then, the CPU 301 obtains the number of cells N3 included in the region A5 and the number of cells N4 included in the region A6 (S115). N3 is comparable to the number of cells having an amount of DNA equal to or greater than that of a normal cell in the S phase. In other words, N3 is comparable to the number of cells having an amount of DNA exceeding the amount of DNA of a normal cell in the G0 phase or the G1 phase. N4 is comparable to the number of cells whose amount of DNA is 2C. In other words, N4 is comparable to the number of cells having the same amount of DNA as that of a normal cell in the G0 phase or the G1 phase.

The value at the left end of the region A5 is set to be the upper limit value in a range of the amount of DNA detected, in the analyzer 1, as the amount of DNA of a normal cell whose cell cycle is in the G0/G1 phase. The right end of the region A5 is set so as to include all cells in the right direction. The value at the right end of the region A6 is set as a value that differentiates normal cells in G0 and G1 phases and normal cells in S phase according to the amount of DNA. Specifically, it is assumed that a value V20 is comparable to the amount of DNA of a normal cell whose cell cycle is in the G0 phase or the G1 phase. V21 and V22 are set such that V20 is included in a range from V21 to V22, and the width of the range from V21 to V22 is a predetermined width A. In the present embodiment, the region A5 and the region A6 are set so as to be adjacent to each other at the value V22.

The CPU 301 determines whether the canceration ratio N3/N4 is greater than or equal to the threshold s4 set in S110 or S111 (S116). When the canceration ration N3/N4 is greater than or equal to the threshold s4 (S116: YES), the CPU 301 determines canceration is positive. When the canceration N3/N4 is smaller than the threshold s4 (S116: NO), the CPU 301 determines canceration is negative.

If canceration is positive (S116: YES), the CPU 301 makes the display unit 32 show an indication that retest is necessary (S117). As shown in FIG. 12B, a dialogue box D2 indicating "retest is necessary" is displayed on the display unit 32. On the other hand, when canceration is negative (S116: NO), the CPU 301 makes the display unit 32 show an indication that retest is unnecessary (S118). As shown in FIG. 12C, a dialogue box D3 indicating "retest is unnecessary" is displayed on the display unit 32. Then, the analysis process by the data processing device 3 ends.

Figure 12D:
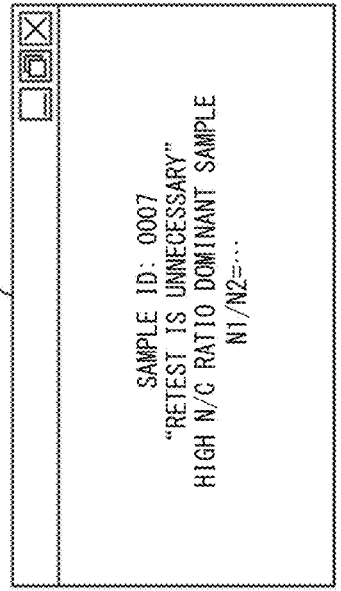
Figure 12B:
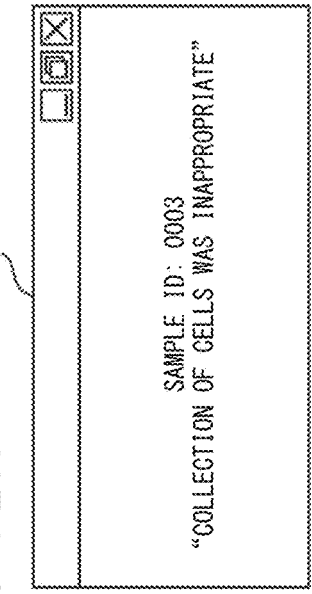
Figure 12C:
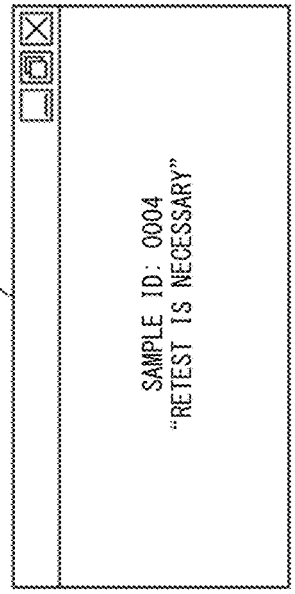
Figure 12E:
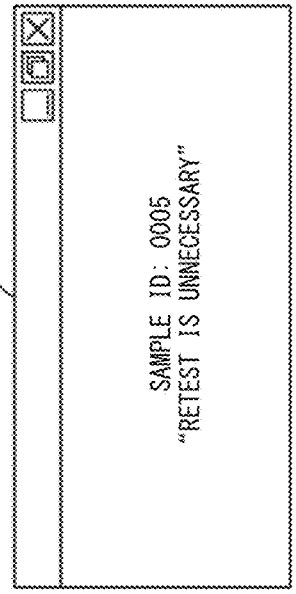

The dialogue boxes D2 and D3 may additionally include the relative amount of the target cells as shown in FIGS. 12D and 12E. Dialogue box D4 shown in FIG. 12D includes "low N/C ratio dominant sample" indicating that the ratio N1/N2 is smaller than s2, and the calculated ratio N1/N2. Dialogue box D5 shown in FIG. 12E includes "high N/C ratio dominant sample" indicating that the ration N1/N2 is greater than or equal to s2 and the calculated ratio N1/N2.

FIG. 13 shows determination results obtained in the present embodiment and comparative example. Comparative example shows a determination result wherein Vsh2 is always applied as the threshold s4. Present embodiment shows a determination result wherein one of Vsh1 and Vsh2 is applied as the threshold s4.

In each case of the comparative example and the present embodiment, the same sample group was subjected to the determination. As shown in the condition in FIG. 13, the total number of samples of the sample group subjected to the determination was 1020. Among them, the number of samples determined as positive in biopsy was 54 and the number of samples determined as negative in biopsy was 966. In FIG. 13, the sensitivity indicates a ratio of the number of samples determined as positive as a result of the determination, relative to the number of samples determined as positive by biopsy. The specificity indicates a ratio of the number of samples determined as negative as a result of the determination, relative to the number of samples determined as negative by biopsy.

In the case of the comparative example, the sensitivity was 98%, and the specificity was 73%. On the other hand, in the present embodiment, the ratio N1/N2 was smaller than s3 in 237 samples. To those, the threshold s4 was set to Vsh1. The sensitivity was 100% and the specificity was 80%. The ratio N1/N2 was greater than or equal to s3 in 783 samples. To those, the threshold s4 was set to Vsh2. The sensitivity was 98% and the specificity was 78%. Thus, the sensitivity was 98% and the specificity was 78% in total. Specificity was 5% higher than the comparative example. Thus, in the present embodiment, compared with the comparative example, accuracy of determination of canceration can be improved.

In the present embodiment, the threshold s4 to be used in determination of canceration is adjusted in accordance with the relative amount of target cells having a large N/C ratio included in the measurement specimen. Accordingly, even if amount of target cells included in the measurement specimen varies, the threshold s4 is appropriately adjusted. Thus, the canceration ratio N3/N4 can be evaluated by use of an appropriate threshold s4, and thus, accuracy of determination of canceration can be increased.

In the present embodiment, single epithelial cells included in the measurement specimen are plotted on the first histogram, and the ratio N1/N2 is obtained based on the number of cells N1 included in the region A3 and the number of cells N2 included in the region A4 of the first histogram as the relative amount of target cells. Accordingly, the balance between target cells and the other epithelial cells included in the measurement specimen can be well evaluated. Thus, in S109 to S111, appropriate threshold s4 can be set.

In the present embodiment, extracted target cells are plotted on the second histogram, and on the second histogram, a ratio N3/N4 is obtained based on the number of cells N3 included in the region A5 and the number of cells N4 included in the region A6. This ratio reflects the proportion of cells whose cell cycle is in the S phase or the G2/M phase. Thus, by comparing this ratio with the threshold s4, canceration of cells can be determined.

In the present embodiment, when determination of canceration is positive (S116: YES), as information regarding canceration of cells, the dialogue box D2 indicating that retest is necessary is displayed on the display unit 32 (S117). Accordingly, the operator can smoothly take measures thereafter by conducting, among others, biopsy for the subject from whom the sample was collected.

In the present embodiment, the dialogue box D1 indicating that collection of parabasal cells was inappropriate is displayed on the display unit 32 (S108), when the number of target cells N1 having a large N/C ratio is smaller than the threshold s1 (S106: YES), and when the ratio N1/N2 is smaller than the threshold s2 and the sum N1+N2 is smaller than the threshold s3 even when N1 is greater than or equal to the threshold s1 (S107: YES). In these cases, determination of canceration (S116) is not performed, and output of information regarding canceration of cells (S117, S118) is not performed. Thus, low reliability result is prevented to be outputted.

In the present embodiment, in S117 and S118, relative amount of target cells is displayed together with determination result of canceration of cells as shown in the dialogue boxes D4 and D5. Accordingly, the operator can understand the condition of tissue collected from the subject, and based on this, the operator can evaluate information regarding canceration of cells.

The embodiment has been described. However, the present disclosure is not limited to the above embodiment, and various modifications can be made to the embodiment other than the above.

For example, epithelial cells of the uterine cervix are exemplified as cells to be analyzed in the above embodiment. However, other epithelial cells of buccal cells, bladder, pharynx, and the like, and furthermore, epithelial cells of organs may be the target of analysis, and determination of canceration of these cells may be performed.

In the above embodiment, the threshold s4 is selected from Vsh1 and Vsh2. However, based on the ratio N1/N2, the threshold s4 may be selected from three or more options. Still alternatively, the threshold s4 may be calculated via a function using the ratio N1/N2. In this case, the threshold s4 is adjusted more finely, and thus, accuracy of determination of canceration may be increased.

In the above embodiment, the ratio N1/N2 is exemplified as the relative amount of target cells. Other than this, however, the relative amount of the target cells may be the difference N1−N2. In this case, for example, depending on whether the difference N1−N2 exceeds a predetermined threshold, the threshold s4 to be used in determination of canceration is adjusted. Alternatively, the relative amount of the target cells may be the mode of the first histogram, that is, a value of the N/C ratio at which the peak of the first histogram exists. In this case, for example, depending on whether the position of the mode exceeds a predetermined threshold, the threshold s4 to be used in determination of canceration is adjusted. Alternatively, cells are plotted on a scattergram having two axes of cell nucleus size N and cell size C, and the slope of an approximation curve based on the plotted particles may be used as the relative amount of target cells. In this case, for example, depending on whether the slope exceeds a predetermined threshold, the threshold s4 to be used in determination of canceration is adjusted. Alternatively, the relative amount of target cells may be represented by a parameter indicating how broad the first histogram is, such as a coefficient of variation of the first histogram. The relative amount of target cells may be obtained through image analysis based on an image showing how many target cells are included in the measurement specimen. Alternatively, distribution information may be obtained through microscopy.

In the above embodiment, the first histogram showing the number of cells in accordance to the N/C ratio is created, and as relative amount of target cells, the ratio N1/N2 is calculated. Other than this, however, relative amount of target cells may be obtained by evaluating cell nucleus size N and cell size C separately.

In the above embodiment, target cells are extracted based on the N/C ratio. However, other embodiments may be employed. For example, target cells may be extracted only based on cell size C.

FIG. 14A is a histogram showing, with respect to the sample whose sample ID is 1 shown in FIGS. 11A and 11C, the number of cells in accordance with cell nucleus size N and cell size C. FIG. 14B is a histogram showing, with respect to the sample whose sample ID is 2 shown in FIGS. 11B and 11D, the number of cells in accordance with cell nucleus size N and cell size C.

The interval in the horizontal axis direction between the mode of cell nucleus size N and the mode of cell size C is small in FIG. 14A but large in FIG. 14B. Thus, for example, the interval of the modes can be used as relative amount of target cells. In this case, depending on whether this interval exceeds a predetermined threshold, the threshold s4 to be used in determination of canceration is adjusted.

In the above embodiment, the regions A3 and A4 are set as shown in FIGS. 11A and 11B, and the regions A5 and A6 are set as shown in FIGS. 11C and 11D. Other than this, however, the ranges of the regions A3 to A6 may be changed as appropriate from the viewpoint of sensitivity and specificity.

FIG. 15A shows a state where the boundary at the right end of the region A3 has been moved in the right direction. FIG. 15B shows a state where both the upper limit and the lower limit of the region A3 have been eliminated. In this manner, from the viewpoint of sensitivity and specificity, the boundaries at the right end and the left end of the region A3 may be set as appropriate in the left-right direction. Similarly, the boundaries at the right end and the left end of the region A4 may also be set as appropriate in the left-right direction. A gap may be provided between the regions A3 and A4. Alternatively, a part of the region A3 and a part of the region A4 may overlap each other.

FIG. 15C shows a state where the boundary at the right end of the region A6 has been moved in the left direction. The value V21 at the left end and a value V23 at the right end of the region A6 in FIG. 15C are set such that V20 is included in the range from V21 to V23, and the width of the range from V21 to V23 is B which is smaller than the width A in FIGS. 11C and 11D. FIG. 15D shows a state where the boundary at the left end of the region A5 has been moved in the left direction. The value V24 at the left end of the region A5 in FIG. 15D is set so as to be greater than V20 and smaller than V22, when V20 is included in the range from V21 to V22 and the width of the range from V21 to V22 is set to be A. In this manner, from the viewpoint of sensitivity and specificity, the boundaries at the right end and the left end of the regions A5 and A6 may be set as appropriate in the left-right direction.

In the above embodiment, in S116, whether the value of N3/N4 is greater than or equal to the threshold s4 is determined. Other than this, however, whether the value of N4/N3 is smaller than or equal to a threshold 1/s4 may be determined.

In the above embodiment, the width of the waveform of the fluorescence signal is defined as cell nucleus size N, and the width of the waveform of the forward scattered light signal is defined as cell size C. Other than this, however, the area of the waveform of the fluorescence signal may be defined as cell nucleus size N, and the area of the waveform of the forward scattered light signal may be defined as cell size C. It should be noted that, when a cell having a shape long in a predetermined direction flows in the flow cell, the cell size is accurately represented by use of the width of the waveform of the forward scattered light signal. Thus, preferably, as in the above embodiment, the width of the waveform of the forward scattered light signal is defined as cell size C.

In the above embodiment, determination of appropriateness of collection of cells is performed in S106 and S107. However, determination of appropriateness of collection of cells is not limited to determination in S106 and S107, and may employ another determination.

In the above embodiment, in the dialogue boxes D1 to D5, indication that collection of parabasal cells was inappropriate, indication that retest is necessary, and indication that retest is unnecessary are displayed, and the dialogue boxes D1 to D5 are displayed on the display unit 32. Other than this, however, these indications may be outputted as alarm sound from a speaker provided in the data processing device 3.

In the above embodiment, an example in which the dialogue boxes displayed in S117 and S118 also include relative amount of target cells included in the measurement specimen is shown in FIGS. 12D and 12E. However, instead such information, the first histogram as shown in FIGS. 11A and 11B may be displayed.

In the above embodiment, the CPU 301 of the data processing device 3 obtains, based on the respective signals, FSC, SSC, and SFL, received from the measurement apparatus 2, characteristic parameters such as the width of the waveform of the forward scattered light signal, the width of the waveform of the fluorescence signal, and the area of the waveform of the fluorescence signal. Other than this, however, these characteristic parameters may be obtained by the measurement control unit 25 of the measurement apparatus 2.

In addition to the above, various modifications of the embodiments may be made as appropriate without departing from the scope of the technical idea defined by the claims.

What is claimed is:

1. A cell analysis method comprising:
performing flow cytometry to measure cell parameters of each sampled cell of a plurality of sampled cells collected from epithelial tissues;
receiving, by a communication interface, the cell parameters of the plurality of sampled cells, wherein the cell parameters include at least a first parameter representing a cell size (C) and a second parameter representing a cell nucleus size (N), wherein the sampled cells are analyzed by a measurement apparatus using a cytometer to obtain the cell parameters;
calculating, by a CPU, a N/C ratio of each sampled cell of the plurality of sampled cells based on the first and second parameters, wherein the N/C ratio represents a relative size of a nucleus in each sampled cell with respect to the cell size (C) of the corresponding sampled cell;
comparing, by the CPU, a first threshold (V11) to the N/C ratio of each sampled cell of the plurality of sampled cells to identify target cells in the plurality of sampled cells having N/C ratios equal to or higher than the first threshold (V11) and non-target cells in the plurality of sampled cells having N/C ratios lower than the first threshold (V11), wherein the target cells have nucleuses having relative sizes being larger than relative sizes of nucleuses of the non-target cells in relation to sizes of their cytoplasm, and wherein the target cells comprise parabasal cells in the epithelial tissues;
counting, by the CPU, a number (N1) of the target cells and a number (N2) of the non-target cells;
classifying, by the CPU, the target cells into at least a first group of cells and a second group of cells according to their amounts of DNA, wherein the cells in the first group each have a greater amount of DNA than the cells in the second group;
counting, by the CPU, a number (N3) of the first group of cells and a number (N4) of the second group of cells and calculating a ratio (N3/N4) of the number (N3) of the first group of cells to the number (N4) of the second group;
comparing, by the CPU, a second threshold (s4) to the ratio (N3/N4) to evaluate pathology of the epithelial tissues such that an evaluation result provides an indication of the presence of cancer suspected cells in the epithelial tissues when the ratio (N3/N4) is equal to or larger than the second threshold (s4);
varying the second threshold (s4), by the CPU, according to a proportion of the target cells in the plurality of sampled cells, wherein the proportion is calculated based on the number (N1) of the target cells and the number (N2) of the non-target cell, to improve a specificity of the determination of the presence of cancer suspected cells in the epithelial tissues compared to not varying the second threshold (s4) according to the proportion; and
prompting a retest of the epithelial tissue by performing flow cytometry on a second plurality of sampled cells collected from the epithelial tissue when the ratio (N3/N4) is greater than or equal to the second threshold (s4).

2. The cell analysis method of claim 1, wherein the proportion of the target cells in the plurality of sampled cells is a ratio of the number (N1) of the target cells with respect to the number (N2) of the non-target cells.

3. The cell analysis method of claim 1, wherein classifying the target cells into at least the first group of cells and the second group of cells comprises classifying, by the CPU, the target cells as the first group whose amounts of DNA are equivalent to those of DNA that fall in cell cycle of G0 to G1 phases and classifying the target cells as the second group whose amounts of DNA are greater than those of DNA that fall in the cell cycle of G0 to G1 phases.

4. The cell analysis method of claim 1, further comprising:
applying, by the CPU, a third threshold (s1) to the number (N1) of the target cells to determine whether the number (N1) of the target cells is sufficiently large for pathologic evaluation of the epithelial tissues; and
aborting, by the CPU, the pathologic evaluation of the epithelial tissues responsive to a determination by the CPU that the number (N1) of the target cells is not sufficiently large for the pathologic evaluation of the epithelial tissues.

5. The cell analysis method of claim 1, further comprising outputting results of the pathologic evaluation of the epithelial tissues, wherein the results include information on the proportion of the target cells.

6. The cell analysis method of claim 1, further comprising:
introducing a measurement specimen containing the plurality of sampled cells collected from the epithelial tissues into a flow cell;
irradiating light to the plurality of sampled cells flowing through the flow cell;
detecting light scattered from the plurality of sampled cells flowing through the flow cell and converting an intensity of the detected scattered light into a series of first signal waveforms; and
detecting fluorescence light scattered from the plurality of sampled cells flowing through the flow cell and converting an intensity of the detected scattered fluorescent light into a series of second signal waveforms.

7. The cell analysis method of claim 6, wherein
the first parameter is a width of a first signal waveform; and
the second parameter is a width of a second signal waveform.

8. The cell analysis method of claim 7, wherein an area of the second signal waveform represents an amount of DNA in a sampled cell of the plurality of sampled cells.

9. The cell analysis method of claim 1, wherein the epithelial tissues are epithelial tissues of uterine cervix.

10. A cell analyzer comprising:
a measurement apparatus comprising a cytometer configured to perform flow cytometry to measure cell parameters of each sampled cell of a plurality of sampled cells collected from epithelial tissues; and
a data processing device connected to the cytometer for processing data on the plurality of sampled cells sent from the cytometer, wherein the data processing device comprises a processor programmed to:
receive from the measurement apparatus the cell parameters of the plurality of sampled cells, wherein the cell parameters include at least a first parameter representing a cell size (C) and a second parameter representing a cell nucleus size (N);
calculate a N/C ratio of each sampled cell of the plurality of sampled cells based on the first and second parameters, wherein the N/C ratio represents a relative size of a nucleus in each sampled cell with respect to the cell size (C) of the corresponding sampled cell;
compare a first threshold (V11) to the N/C ratio of each sampled cell of the plurality of sampled cells to identify target cells in the plurality of sampled cells having N/C ratios equal to or higher than the first threshold (V11) and non-target cells in the plurality of sampled cells having N/C ratios lower than the first threshold (V11), wherein the target cells have nucleuses having relative sizes being larger than sizes of nucleuses of the non-target cells in relation to sizes of their cytoplasm, and wherein the target cells comprise parabasal cells in the epithelial tissues;
count a number (N1) of the target cells and a number (N2) of the non-target cells;
classify the target cells into at least a first group of cells and a second group of cells according to their amounts of DNA, wherein the cells in the first group each have a greater amount of DNA than the cells in the second group;
count a number (N3) of the first group of cells and a number (N4) of the second group of cells and calculate a ratio (N3/N4) of the number (N3) of the first group of cells to the number (N4) of the second group;
compare a second threshold (s4) to ratio (N3/N4) to evaluate pathology of the epithelial tissues such that an evaluation result provides an indication of the presence of cancer suspected cells in the epithelial tissues when the ratio (N3/N4) is equal to or larger than the second threshold (s4);
vary the second threshold (s4) according to a proportion of the target cells in the plurality of sampled cells, wherein the proportion is calculated based on the number (N1) of the target cells and the number (N2) of the non-target cells, to improve a specificity of the determination of the presence of cancer suspected cells in the epithelial tissues compared to not varying the second threshold (s4) according to the proportion; and
prompt a retest of the epithelial tissue by performing flow cytometry on a second plurality of sampled cells collected from the epithelial tissue when the ratio (N3/N4) is greater than or equal to the second threshold (s4).

11. The cell analyzer of claim 10, further comprising an output unit operable to output results of the pathologic evaluation of the epithelial tissues, wherein the data processing device is further programmed to operate the output unit to output information on the proportion of the target cells.

12. The cell analyzer of claim 10, wherein the cytometer comprises:
a flow cell through which the plurality of sampled cells collected from the epithelial tissues flow;
a light source operable to irradiate light to the plurality of sampled cells flowing through the flow cell;
a first detector configured to detect light scattered from the plurality of sampled cells flowing through the flow cell and convert an intensity of the detected scattered light into a series of first signal waveforms; and
a second detector configured to detect fluorescence light scattered from the plurality of sampled cells flowing through the flow cell and convert an intensity of the detected scattered fluorescent light into a series of second signal waveforms.

13. The cell analyzer of claim 12, wherein
the first parameter is a width of a first signal waveform; and
the second parameter is a width of a second signal waveform.

14. The cell analyzer of claim 12, wherein the data processing device is programmed to determine an amount of DNA in a sampled cell of the plurality of sampled cells from an area of a corresponding second signal waveform.

15. The cell analyzer of claim 12, wherein the proportion of the target cells in the plurality of sampled cells is a ratio of the number (N1) of the target cells with respect to the number (N2) of the non-target cells.

* * * * *